United States Patent
Tzvetkov

(10) Patent No.: US 9,643,930 B2
(45) Date of Patent: May 9, 2017

(54) SUBSTITUTED INDAZOLE DERIVATIVES AS IN VITRO MAO-B INHIBITORS

(71) Applicant: "NTZ LAB" LTD., Sofia (BG)

(72) Inventor: Nikolay Tzvetkov, Sofia (BG)

(73) Assignee: "NTZ LAB" LTD., Sofia (BG)

( * ) Notice: Subject to any disclaimer, the term of this patent is extended or adjusted under 35 U.S.C. 154(b) by 0 days.

(21) Appl. No.: 14/760,441

(22) PCT Filed: Jun. 5, 2013

(86) PCT No.: PCT/BG2013/000025
§ 371 (c)(1),
(2) Date: Jul. 10, 2015

(87) PCT Pub. No.: WO2014/107771
PCT Pub. Date: Jul. 17, 2014

(65) Prior Publication Data
US 2015/0353504 A1    Dec. 10, 2015

(30) Foreign Application Priority Data

Jan. 14, 2013  (BG) .......................... 111378

(51) Int. Cl.
| | | |
|---|---|---|
| C07D 231/56 | (2006.01) | |
| C07D 401/12 | (2006.01) | |
| A61K 31/4045 | (2006.01) | |
| A61K 31/416 | (2006.01) | |

(52) U.S. Cl.
CPC ........ *C07D 231/56* (2013.01); *A61K 31/4045* (2013.01); *A61K 31/416* (2013.01); *C07D 401/12* (2013.01)

(58) Field of Classification Search
None
See application file for complete search history.

(56) References Cited

U.S. PATENT DOCUMENTS

2011/0152321 A1    6/2011  Lawson et al.

FOREIGN PATENT DOCUMENTS

| EP | 1 403 255 A1 | 3/2004 |
|---|---|---|
| WO | 2011/076786 A1 | 6/2011 |

OTHER PUBLICATIONS

Nakkady et al., "New indole, aminoindole and pyranoindole derivatives with anti-inflammatory activity," Unbound Medline, Bollettino chimico farmaceuticpo 139:2 pp. 59-66, 2000.

Demetrio Raffa et al., "N-(Indazolyl)benzamido Derivatives as CDK1 Inhibitors: Design, Synthesis, Biological Activity, and Molecular Docking Studies," Arch. Pharm. Chem. Life Sci. 2009, 342, pp. 265-273.

Alfred W. J. Bach et al., "cDNA cloning of human liver monoamine oxidase A and B: Molecular basis of differences in enzymatic properties," Proc. Natl. Acad. Sci. USA, vol. 85, pp. 4934-4938, Jul. 1988.

Andrea M. Cesura et al., "The new generation of monoamine oxidase inhibitors," Progress in Drug Research 38, 1992, pp. 171-297.

(Continued)

*Primary Examiner* — Anna Pagonakis
(74) *Attorney, Agent, or Firm* — Baker Hostetler LLP

(57) ABSTRACT

Substituted indazole or imidazole derivatives of formula I as an in vitro selective and reversible MAO-B inhibitors and for use in the prevention and treatment of neurodegenerative disorders such as Parkinson's disease, Alzheimer's disease and dementia.

1 Claim, 6 Drawing Sheets

(56) References Cited

OTHER PUBLICATIONS

Andrew Holt et al., "A Continuous Spectrophotometric Assay for Monoamine Oxidase and Related Enzymes in Tissue Homogenates," Analytical Biochemistry 244, Article No. AB969911, pp. 384-392, 1997.

Demetrio Raffa et al., "Synthesis and antifungal activity of new N-(1-phenyl-4-carbetoxypyrazol-5-yl)-, N-(indazol-3-yl)- and N-(indazol-5-yl)-2-iodobenzamides," Il Farmaco 57, 2002, pp. 183-187.

Shaheen E. Lakhan, "From a Parkinson's disease expert: Rasagiline and the Future of Therapy," Molecular Neurodegeneration, 2(13), 2007.

Roberto Maj et al., "PNU-151774E protects against kainate-induced status epilepticus and hippocampal lesions in the rat," European Journal of Pharmacology 359, 1998, pp. 27-32.

Antonio Marzo et al., "Pharmacokinetics and pharmacodynamics of safinamide, a neuroprotectant with antiparkinsonian and anticonvulsant activity," Pharmacological Research 50, 2004, pp. 77-85.

Palhagen et al., "Selegiline slows the progression of the symptoms of Parkinson disease," Neurology 2006, 66(8), pp. 1200-1206.

Jacobus P. Petzer et al., "Inhibition of Monoamine Oxidase B by Selective Adenosine A2A Receptor Antagonists," Bioorganic & Medicinal Chemistry 11, 2003, pp. 1299-1310.

P. Riederer et al., "Selegiline's neuroprotective capacity revisited," Journal of Neural Transmission, 2003, 110(11), pp. 1273-1278.

Hitoshi Takami et al., "Indole and Benzimidazole Derivatives as Steroid 5α-Reductase Inhibitors in the Rat Prostate," Bioorganic & Medicinal Chemistry 6, 1998, pp. 2441-2448.

"Dementia: A Public Health Priority," World Health Organization, Alzheimer's Disease International, 2012.

Moussa B. H. Youdim et al., "New Directions in Monoamine Oxidase A and B Selective Inhibitors and Substrates," Biochemical Pharmacology, vol. 41, No. 2, pp. 155-162, 1991.

Moussa B. H. Youdim et al., "Rasagiline [N-propargyl-1R(+)-aminoindan], a selective and potent inhibitor of mitochondrial monoamine oxidase B," British Journal of Pharmacology 132, 2001, pp. 500-506.

Franz Oesch et al., "Xenobiotic Metabolism," Toxicology, Academic Press, San Diego 1999, pp. 83-109.

Franz Oesch et al., "Detoxication Strategy of Epoxide Hydrolase—The Basis for a Novel Threshold for Definable Genotoxic Carcinogens," Nonlinearity in Biology, Toxicology, and Medicine, vol. 2, No. 1, Jan. 2004, pp. 21-26.

SUBSTITUTED INDAZOLE DERIVATIVES AS IN VITRO MAO-B INHIBITORS

CROSS-REFERENCE TO RELATED APPLICATIONS

This application is a National Stage of International patent application PCT/BG2013/000025, filed on Jun. 5, 2013, which claims priority to foreign Bulgarian patent application No. 111378, filed on Jan. 14, 2013 the disclosures of which are incorporated by reference in their entirety.

TECHNICAL FIELD OF INVENTION

The present invention relates to substituted indazole derivatives and their salts, isomers or mixtures thereof, that are useful as in vitro selective and reversible MAO-B inhibitors.

BACKGROUND

The monoamine oxidases (MAO, EC 1.4.3.4) are anzymes responsible for the oxidation of biogenic amines. Due to their important role in the neurotransmitters inactivation, the dysfunction of MAO enzymes (increased levels of MAO activity) is associated with a number of mental and neurological disorders such as depression, anxiety disorders and migraine.

The MAO enzymes exist in two isoforms, MAO-A and MAO-B, which have approximately 70% amino acid sequence identity (Oesch and Arand, *Toxicology*, Academic Press, San Diego USA, 1999) and differing in substrate specificity and tissue distribution (Bach et al., *Proc. Natl. Acad. Sci. USA* 85, 4934-4938, 1988). The MAO-B enzyme is found in high levels in the liver, platelets, and especially in brain (Cesura and Pletscher, *Prog. Drug Res.* 38, 171-297, 1992). The natural substrates for MAO-B are preferentially phenylethylamine and tyramine. Another important substrate for MAO-B is the tertiary amine 1-Methyl-4-phenyl-1,2,3,6-tetrahydropyridine (MPTP) which is metabolized by MAO-B in neurons. It is known, that the product of this metabolic reaction MPP$^+$ is a Parkinson inducing dopaminergic neurotoxin (Youdim et al., *Biochem. Pharmacol.* 41, 155-162, 1991; Petzer et al., *Bioorg. Med. Chem.* 11, 1299-1310, 2003).

It is known, that MAO inhibitors (MAOI) are substances that inhibit the MAO activity and due to their selectivity of the MAO receptor, they can be selective or non-selective. MAO-A inhibitors are therapeutically useful as antidepressants, whereas MAO-B inhibitors can be used in the monotherapy or in combination with levodopa (L-DOPA) for the treatment of Alzheimer's Disease (AD), Parkinson's Disease (PD) and other neurological diseases associated with the degeneration of dopaminergic neurons (Pålhagen et al., *Neurology*, 66, 1200-1206, 2006). The World Health Organisation (WHO) reported that 36.5 million people worldwide are living with different types of dementia including Alzheimer's Disease and Parkinson's Disease Dementia (PDD)—with upward tendency (WHO, *Dementia: a public health priority*, 2012). These neurodegenerative diseases are the most common types of dementia, characterized by a decreased level of dopamine which is mediated by the degeneration of dopaminergic neurons in substantia nigra.

The current therapy of AD and PD is primarily focused on the treatment of the symptoms affecting the quality of live in patients. Since these symptoms are caused by a decreasing of dopamine levels in the brain, the most therapeutic drugs are based on dopamine replacement using dopamine-enhancing approach such as levodopa or dopamine agonists to stimulate the dopamine receptors. The MAO-B inhibitors are also used as an alternative therapeutic approach of the dopamine agonists for treatment of neurodegenerative diseases. For example, both selegiline (Riederer and Lachenmayer, *J. Neural Transm.*, 110 (11), 1273-8, 2003) and rasagiline (Lakhan, *Molecular Neurodegeneration*, 2(13), 2007) are used as irreversible inhibitors for the treatment of PD. The therapeutic effect of MAO-B inhibitors is provided by blocking of monoamine oxidase B (MAO-B) enzymes in the brain.

Patent application EP1403255 discloses a number of substituted 1H-indazole derivatives, including 1H-indazolecarboxamide and 1H-indazolemethyleneamine. These compounds and prodrugs thereof are described as Rho kinase inhibitors (ROCK-II inhibitor, ROC alpha inhibitor) and are useful as prophylactic or therapeutic agents for urinary incontinence.

It is therefore an object of the present invention to provide in vitro selective and reversible MAO-B inhibitors with IC$_{50}$ values in the subnanomolar range for the prevention and treatment of acute and chronic neurological disorders, cognitive and neurodegenerative diseases.

Description

The present invention relates to the use of substituted indazole derivatives represented by the formula I:

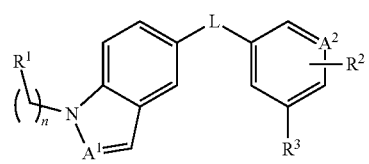

wherein L is —CO—NH— or —CH=N—;
A$^1$ is —N, —CH or N—(CH$_2$)$_n$R$^1$;
A$^2$ is —N or —CH;
R$^1$ is a hydrogen atom, or represents branched or unbranched —(C$_1$-C$_3$)-alkyl, —(C$_1$-C$_3$)-alkyl, wherein one, two or three hydrogen atoms may be substituted by a halogen, —(C$_1$-C$_3$)-alkoxy or halogen-(C$_1$-C$_3$)-alkoxy; mono- or dihydroxy-(C$_1$-C$_3$)-alkyl;
R$^2$ and R$^3$ both together or independently from each other are halogen, hydroxy, halogen-(C$_1$-C$_3$)-alkyl, —(C$_1$-C$_3$)-alkoxy, —O—(C$_1$-C$_3$)-alkoxy;
wherein R$^2$ and R$^3$ both together or independently from each other are aryl, aryl substituted by a (C$_3$-C$_5$)-alkyl, when A is —CH;
and wherein R$^2$ and R$^3$ both together or independently from each other are heteroaryl, substituted by a (C$_3$-C$_4$)-alkyl, when A is =N;
and n is 0, 1, 2 or 3, their pharmaceutically acceptable salts, isomers or mixtures thereof as in vitro selective and reversible MAO-B inhibitors with IC$_{50}$ values in subnanomolar range for the manufacture of medicaments for the prevention and treatment of acute and chronic neurological disorders, cognitive and neurodegenerative diseases. In particular, the compounds of formula I are useful for the prevention and treatment of neurodegenerative disorders such as Parkinson's Disease, Alzheimer's Disease and dementia.

In one more preferable embodiment, for the manufacturing of a medicament can be used compounds of formula I selected from the group consisting of:
N-(3,4-Dichlorophenyl)-1H-indazole-5-carboxamide,
N-(3,4-Dichlorophenyl)-1H-indole-5-carboxamide,
N-(3-Chloro-4-methoxyphenyl)-1H-indazole-5-carboxamide,
N-(4-Chloro-3-methoxyphenyl)-1H-indazole-5-carboxamide, N-(3-Chloro-4-hydroxyphenyl)-1H-indazole-5-carboxamide,
N-(4-Chloro-3-hydroxyphenyl)-1H-indazole-5-carboxamide,
N-(3,4-Dimethoxyphenyl)-1H-indazole-5-carboxamide,
N-(3,5-Dichlorophenyl)-1H-indazole-5-carboxamide,
N-(3-Chloro-4-fluorophenyl)-1H-indazole-5-carboxamide,
N-(4-Chloro-3-fluorophenyl)-1H-indazole-5-carboxamide,
N-(3,4-Difluorophenyl)-1H-indazole-5-carboxamide,
N-(5,6-Dichloropyridin-3-yl)-1H-indazole-5-carboxamide,
N-(3,4-Dichlorophenyl)-1-methyl-1H-indazole-5-carboxamide,
N-(3,4-Dichlorophenyl)-2-methyl-2H-indazole-5-carboxamide,
mixture of N-(3,4-Dichlorophenyl)-1-methyl-1H-indazole-5-carboxamide and
N-(3,4-Dichlorophenyl)-2-methyl-2H-indazole-5-carboxamide,
N-(3,4-Dichlorophenyl)-1-methyl-1H-indole-5-carboxamide,
N-(3-Chloro-4-fluorophenyl)-1-methyl-1H-indazole-5-carboxamide,
N-(3-Chloro-4-fluorophenyl)-2-methyl-2H-indazole-5-carboxamide,
N-(3,4-Difluorophenyl)-1-methyl-1H-indazole-5-carboxamide,
N-(3,4-Difluorophenyl)-2-methyl-2H-indazole-5-carboxamide,
N-(3,4-dichlorophenyl)-1-(2-methoxyethyl)-1H-indazole-5-carboxamide,
(E)-N-((1H-indazol-5-yl)methylene)-3,4-dichloroaniline,
(E)-N-((1H-indazol-5-yl)methylene)-4-chloro-3-fluoroaniline,
(E)-N-((1H-indazol-5-yl)methylene)-3-chloro-4-fluoroaniline,
(E)-N-((1H-indazol-5-yl)methylene)-5,6-dichloropyridin-3-amine,
(E)-3,4-dichloro-N-((1-methyl-1H-indazol-5-yl)methylene)aniline
and their pharmaceutically acceptable salts.

The compounds within this invention represented by the general formula I may be used for preparing of radiolabeled [³H]-analogues of the compounds of the present invention, which can be useful as MAO-B radioligands in radioligand binding studies related to MAO-B inhibition.

The compounds of formula I may be prepared by any process known by one skilled in the art. In one preferred embodiment, the compounds of the present invention are prepared following the synthetic methods showed in Scheme 1:

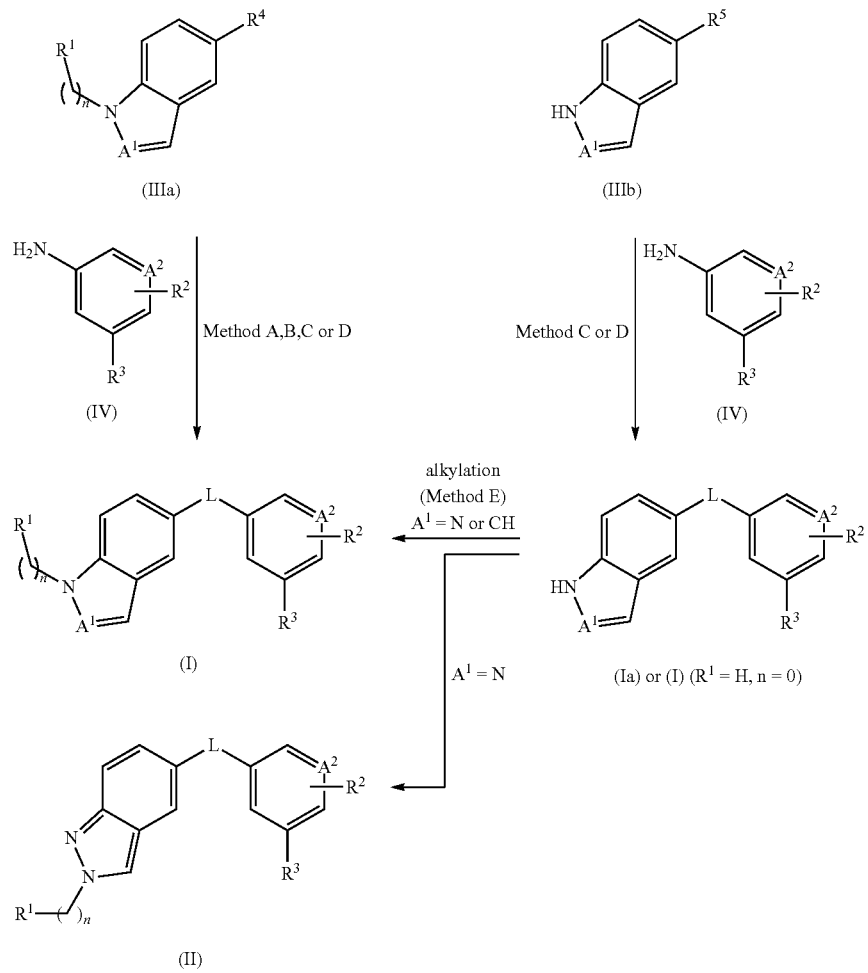

wherein $A^1$, $A^2$, $R^1$, $R^2$, $R^3$ and L have the above meanings and wherein $R^4$ and $R^5$ are carboxylic or substituted carboxylic group or an aldehyde group.

According to method A and C, an amide bond is formed by the reaction of the differently substituted carboxylic acids with general formula IIIa and IIIb with the amino group of the corresponding disubstituted anilines or aminopyridines with general formula IV. The amide coupling reaction can be conducted in the presence of a base such as Hünig's base (N,N-diisopropylethylamine, DIPEA) and a condensation agent such as e.g. O-(benzotriazol-1-yl)-N,N,N',N'-tetramethyluronium hexafluorophosphate (HBTU), O-(benzotriazol-1-yl)-N,N,N',N'-tetramethyluronium tetrafluoroborate (TBTU), or other benzotriazol derivatives. The reaction can be conducted in suitable solvent such as methanol or more preferably in acetonitrile (ACN) at room temperature over night (method A). Fort the amide bond forming step another condensation reagents like carbodiimides such as e.g. N,N-dicyclohexylcarbodiimide (DCC) and N-(3-dimethylaminopropyl)-N'-ethylcarbodiimide hydrochloride (EDC) or other suitable coupling reagents and methods can be used. This step can be conducted at room temperature in the presence of methanol, N,N-dimethylformamide (DMF) or other suitable solvents (method C).

Another method B to prepare compounds of formula I involves the use of activated carboxylic acids, e.g. acid chloride intermediates of formula IIIa. This method is described by Raffa et al. (*Arch. Pharm. Chem. Life Sci.*, 342, 265-273, 2009; *Il Farmaco* 57, 183-187, 2002).

For the preparation of a compound of formula I wherein L has the meaning of —CH=N—, the optionally substituted aldehyde with general formula IIIa can be condensed with an amino group of the aniline or aminopyridine IV. The reaction is carried out in the presence of catalytic amount of acid such as e.g. acetic acid by using suitable solvent such as ethanol at room temperature or preferably under reflux. The reaction takes from several minutes to 24 hours (method D). As described in the international patent application WO2011/076786, the product of this process is only possible on condition that the other amino group containing reagent, e.g. an nitrogen in case of aminopyridine, is stable under the described conditions.

In accordance with the present invention wherein L is —CO—NH— and —CH=N—, $A^1$, $A^2$, $R^1$, $R^2$ and $R^3$ are defined as mentioned above, the N-alkylated compounds of the formula I can be optionally prepared via intermediates thereof, e.g. compounds of general formula Ia, as shown in Scheme 1.

Intermediates of formula Ia wherein $R^1$ is hydrogen and n is 0 can be defined as final compounds. The compounds of formula Ia can be obtained as described above by using method C or D. To introduce an additional substituent in the compounds of general formula I, e.g. an alkyl group in the position 1 or 2, more preferably in the position N1, the intermediates Ia can be alkylated with an appropriate alkylating reagent such as alkylhalide or methyl methanesulfonate (MMS). The reaction occurs in the presence of an excess of a base such as potassium carbonate in suitable solvent such as N,N-dimethylformamide (DMF) at room temperature. Depending on the alkylating reagent, the reaction can be achieved at temperatures between 60° C. and 90° C. for 3 up to 26 hours (alkylation method E). The conversion of the starting material is detected by TLC. The mixture of the N1-/N2-alkyl products with general formula I can be separated by column chromatography on silica gel (eluent: dichloromethane/methanol 9:1).

According to method E, compounds selected from the formula I of the present invention can be radiolabeled by an alkylation reaction with the corresponding radiolabeled alkylating reagent, e.g. methylation with tritium-labeled methyl methanesulfonate [$^3$H]MMS.

The pharmaceutically acceptable salts of the compounds of formula I may be prepared by adding free organic and inorganic acids. Among organic acids, trifluoroacetic acid, acetic acid, oxalic acid, or lysine acid may be used to form pharmaceutically acceptable salts of the compounds represented by the formula I of the present invention. Among inorganic acids, hydrochloric acid, hydroboronic acid, sulphuric acid, or phosphoric acid may be used for the preparation of the pharmaceutically acceptable salts thereof.

The MAO-A and MAO-B enzyme activity of the compounds was estimated following an assay adapted from the method described by Holt et al. (*Anal. Biochem.*, 142, 627-637, 1997). The MAO experiments were performed using a fluorescence-based detection of resorufin, obtained by a reaction of released from the biological sample $H_2O_2$ with 10-acetyl-3,7-dihydroxyphenoxazine (ADHP) in the presence of a peroxidase (horseradish peroxidase-coupled reaction, HRP).

The inhibitory activity of the compounds of general formula I was investigated at rat and human MAO-A and MAO-B using rat and human MAO-A and MAO-B enzymes, respectively.

To perform rat MAO-A and MAO-B experiments, a preliminary membrane preparation of mitochondrial-enriched rat livers isolated from male Sprague-Dawley rats (Harlan Sprague Dawley, Dublin, US) was required. As sources for recombinant human MAO-A and MAO-B enzymes were used microsomal products, prepared from baculovirus-infected insect cells expressing human MAO-A (Sigma-Aldrich, M7316) and human MAO-B (Sigma-Aldrich, M7441), respectively.

To estimate MAO-A and MAO-B inhibitory activity of the compounds of formula I at rat MAO-A and MAO-B as well as at human MAO-A and MAO-B, the corresponding test compound was dissolved in 100% DMSO and subsequently added to the appropriate enzyme solution containing rat liver mitochondria (rat MAO-A and MAO-B) or recombinant human protein (for determination of human MAO-A and MAO-B) in sodium phosphate buffer. The test sample was incubated for 30 min at room temperature prior to the addition of Amplex® Red reagent (Invitrogen A12214) using for the fluorescence-based measuring of MAO inhibitory activity. The enzymatic reaction started by the addition of the substrate p-tyramine. The fluorescence measurements were performed over a period of 45 min using a microplate fluorescence reader (excitation at 544 nm and emission at 590 nm). $IC_{50}$ values were determined from inhibition curves obtained using different inhibitor concentrations in triplicate within the same experiment, by fitting data to a four parameter logistic equation using computer program.

The time-dependent inhibition studies of the compounds selected from the formula I were deduced at their corresponding $IC_{80}$ values versus p-tyramine (estimated at 150 µM final concentration) in the test samples with and without enzyme inhibitor. The enzyme activity of the test compounds was measured for (20-30) 22 min in the presence of low substrate concentration of following by a gradually increasing of the substrate concentration of p-tyramine. A reactivation of MAO-B activity was observed after increasing of the substrate concentration. The reactivation of the enzyme was monitored by fluorescence measurements over a period of 5 hours. In the case of the test compounds of formula I, an elevated fluorescence can be detected, indicating that the test compounds are reversible MAO-B inhibitors. The irreversible inhibitor selegiline (Youdim et al., *Br. J. Pharmacol.*, 132, 500-506, 2001) and the reversible inhibitor safinamide (Maj et al., *Eur. J. Pharmacol.*, 359, 27-32, 1998; Marzo et al., *Pharmacol. Res.*, 50, 77-85, 2004) were used as reference compounds.

The substituted indazole derivatives of general formula I related to the present invention and their pharmaceutically acceptable salts, isomers or mixtures thereof can be used as ingredients in the form of pharmaceutical preparations with oral or parental administration. The pharmaceutical preparations can be used in the form of hard or liquid dosage forms, prepared in known manner by means of common excipients and techniques.

EXAMPLES

Figure 1:
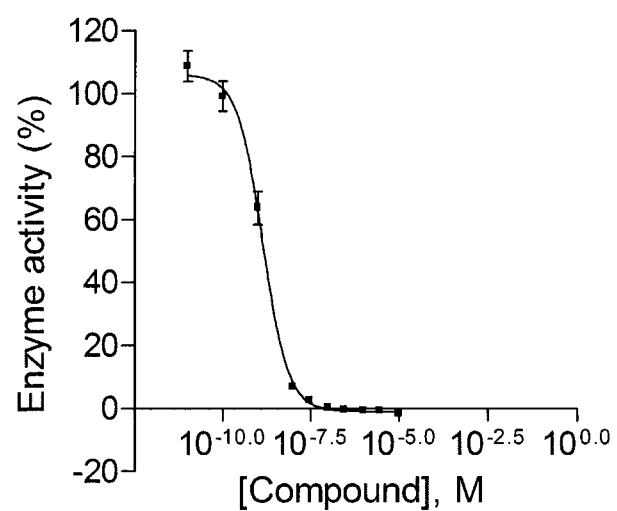
FIG. 1 shows the mean inhibition curve of the rat MAO-B assay using rat liver mitochondria (pre-treated with clorgyline 30 nM) for determination of MAO-B inhibition activity ($IC_{50}$) of N-(3,4-dichlorophenyl)-1H-indazole-5-carboxamide.

The following Examples illustrate methods for the preparation and functional assays for determination of the pharmacological effect of the compounds of formula I according to the present invention. They should not be considered as limiting the scope of the present invention, but merely as being representative thereof:

Example 1

Preparation of N-(3,4-dichlorophenyl)-1H-indazole-5-carboxamide

Method A

A solution of 1H-indazole-5-carboxylic acid (130 mg, 0.8 mmol), 3,4-dichloroaniline (156 mg, 0.96 mmol) and O-(benzotriazol-1-yl)-N,N,N',N'-tetramethyluronium tetrafluoroborate (308 mg, 0.96 mmol) in acetonitrile (5 mL) was treated with N,N-diisopropylethylamine (0.18 mL, 0.96 mmol). The reaction was allowed to stir over night at room temperature. The precipitate formed was filtered, dried at 70° C. and purified by column chromatography on silica gel (eluent: dichloromethane/methanol, 9:1, v/v) to give 25 mg (10%) of the product as a white solid, m.p. 270.8-271.6° C. $^1$H NMR (500 MHz, DMSO-$d_6$) δ (ppm): 7.60 (d, J=8.83 Hz, 1H), 7.65 (d, J=8.83 Hz, 1H), 7.78 (dd, J=2.52/8.83 Hz, 1H), 7.94 (dd, J=1.58/8.83 Hz, 1H), 8.18 (d, J=2.52 Hz, 1H), 8.28 (s, 1H), 8.48 (s, 1H), 10.49 (s, 1H), 13.35 (s, 1H). $^{13}$C NMR (125 MHz, DMSO-$d_6$) δ (ppm): 110.2, 120.3, 121.5, 121.6, 122.5, 125.0, 125.7, 126.8, 130.7, 131.0, 135.2, 139.8, 141.3, 166.2. LC/ESI-MS m/z: negative mode 305 ([M−H]$^−$), positive mode 307 ([M+H]$^+$).

Method B

A solution of 1H-indazole-5-carboxylic acid (162 mg, 1.0 mmol) in N,N-dimethylformamide (0.1 mL) was treated with an excess of oxalyl chloride (0.255 mL, 3.0 mmol). The solution was heated at 80° C. for several minutes until complete conversion. The reaction was stirred for further 30 min at room temperature and then concentrated in vacuo to afford crude acid chloride which was treated with a solution of 3,4-dichloroaniline (162 mg, 1.0 mmol) in pyridine (3 mL). The mixture was stirred at room temperature over night and treated with ice cooled water (10 mL). The orange solid formed was purified by repeated column chromatography on silica gel (eluent: DCM/MeOH, 9:1, v/v) to give 35 mg (11%) of the product as a white solid with an excellent purity.

Method C

A solution of 1H-indazole-5-carboxylic acid (162 mg, 1.0 mmol), 3,4-dichloroaniline (162 mg, 1.0 mmol) and N-(3-dimethylaminopropyl)-N'-ethylcarbodiimide hydrochloride (203 mg, 1.1 mmol) in methanol (5 mL) was stirred over night at room temperature. The reaction was concentrated in vacuo and the residue was treated with a water/ether-mixture (5:1, 30 mL). The mixture was stirred for 30 min at room temperature. The precipitate formed was filtered under reduced pressure and dried at 70° C. The crude product was purified by column chromatography on silica gel (eluent: DCM/MeOH, 9:1, v/v) to give 113 mg (37%) of the product as a white solid.

Example 2

Preparation of N-(3,4-dichlorophenyl)-1H-indole-5-carboxamide

The compound was prepared according to the same procedure of Example 1/Method C by using an amide-coupling of 1H-indole-5-carboxamide with 3,4-dichloroaniline except using of repurification by column chromatography on silica gel (eluent: EtOAc/petroleum ether, 1:1, v/v). Yield 52 mg (17%) as a white solid, m.p. 233.8-234.8° C. $^1$H NMR (500 MHz, DMSO-$d_6$) δ (ppm): 6.59 (m, 1H), 7.46 (t, J=3.16 Hz, 1H), 7.49 (d, J=8.51 Hz, 1H), 7.58 (d, J=8.82 Hz, 1H), 7.72 (dd, J=1.89/8.83 Hz, 1H), 7.79 (dd, J=2.53/8.83 Hz, 1H), 8.20 (d, J=2.21 Hz, 1H), 8.26 (d, J=1.89 Hz, 1H), 10.34 (s, 1H), 11.39 (s, 1H). $^{13}$C NMR (125 MHz, DMSO-$d_6$) δ (ppm): 102.5, 111.3, 120.2, 120.8, 121.1, 121.3, 124.6, 125.2, 127.2, 127.2, 130.6, 130.9, 138.0, 140.1, 167.0. LC/ESI-MS m/z: negative mode 304 ([M−H]$^−$), positive mode 306 ([M+H]$^+$).

Example 3

Preparation of N-(3-chloro-4-methoxy)-1H-indazole-5-carboxamide

The compound was prepared according to the same procedure of Example 1/Method A. Yield 33 mg (11%) as a white solid, m.p. 276.2-277.8° C. $^1$H NMR (500 MHz, DMSO-$d_6$) δ (ppm): 3.84 (s, 3H, 4-MeO), 7.15 (d, J=9.15 Hz, 1H), 7.65 (d, J=8.83 Hz, 1H), 7.68 (dd, J=2.53/8.83 Hz, 1H), 7.94 (dd, J=1.57/8.83 Hz, 1H), 7.97 (d, J=2.52 Hz, 1H), 8.24 (s, 1H), 8.48 (s, 1H), 10.25 (s, 1H), 13.34 (s, 1H). $^{13}$C NMR (125 MHz, DMSO-d$_6$) δ (ppm): 56.3 (OMe), 110.1, 113.0, 120.2, 120.6, 121.3, 122.0, 122.5, 125.7, 127.2, 133.3, 135.1, 141.2, 150.8, 165.7. LC/ESI-MS m/z: negative mode 300 ([M−H]$^−$), positive mode 302 ([M+H]$^+$).

Example 4

Preparation of
N-(4-chloro-3-methoxy)-1H-indazole-5-carboxamide

The compound was prepared according to the same procedure of Example 1/Method A. Yield 34 mg (11%) as a white solid, m.p. 279.6-281.6° C. $^1$H NMR (500 MHz, DMSO-d$_6$) δ (ppm): 3.85 (s, 3H, 4-MeO), 7.36 (d, J=8.82 Hz, 1H), 7.46 (dd, J=2.53/8.83 Hz, 1H), 7.64 (d, J=8.51 Hz, 1H), 7.71 (dd, J=2.21 Hz, 1H), 7.94 (dd, J=1.57/8.82 Hz, 1H), 8.27 (s, 1H), 8.47 (d, J=0.63 Hz, 1H), 10.32 (s, 1H), 13.32 (s, 1H). $^{13}$C NMR (125 MHz, DMSO-d$_6$) δ (ppm): 56.0 (OMe), 105.0, 110.1, 113.0, 115.2, 121.4, 122.5, 125.7, 127.2, 129.7, 135.1, 139.8, 141.2, 154.5, 166.0. LC/ESI-MS m/z: negative mode 300 ([M−H]$^−$), positive mode 302 ([M+H]$^+$).

The compounds of the following Examples 5-12 were obtained according to the same procedure described in Example 1/Method C above an amide coupling of 1H-indazole-5-carboxylic acid with the appropriate aniline or aminopyridine.

Example 5

Preparation of N-(3-chloro-4-hydroxyphenyl)-1H-indazole-5-carboxamide

Yield 169 mg (59%) as a yellowish solid, m.p. 272.2-273.4° C. $^1$H NMR (500 MHz, DMSO-d$_6$) δ (ppm): 6.94 (d, J=8.82 Hz, 1H), 7.50 (dd, J=2.53/8.83 Hz, 1H), 7.62 t (d, J=0.95/8.82 Hz, 1H), 7.85 (d, J=2.53 Hz, 1H), 7.92 (dd, J=1.57/8.82 Hz, 1H), 8.24 (s, 1H), 8.43 (dd, J=0.95/1.58 HZ, 1H), 9.92 (bs, 1H, OH), 10.12 (s, 1H), 13.29 (s, 1H). $^{13}$C NMR (125 MHz, DMSO-d$_6$) δ (ppm): 110.1, 116.5, 119.1, 120.6, 121.2, 122.0, 122.5, 125.7, 127.3, 132.0, 135.0, 141.1, 149.3, 165.6. LC/ESI-MS m/z: negative mode 286 ([M−H]$^−$), positive mode 288 ([M+H]$^+$).

Example 6

Preparation of N-(4-chloro-3-hydroxyphenyl)-1H-indazole-5-carboxamide

Yield 151 mg (53%) as a brownish solid, m.p. 306.6-307.3° C. $^1$H NMR (500 MHz, DMSO-d$_6$) δ (ppm): 7.19 (dd, J=2.52/8.83 Hz, 1H), 7.25 (d, J=8.51 Hz, 1H), 7.62 (td, J=0.95/8.82 Hz, 1H), 7.68 (d, J=2.21 Hz, 1H), 7.92 (dd, J=1.89/8.83 Hz, 1H), 8.25 (s, 1H), 8.45 (dd, J=0.95/1.58 Hz, 1H), 10.16 (bs, 1H, OH), 10.22 (s, 1H), 13.32 (s, 1H). $^{13}$C NMR (125 MHz, DMSO-d$_6$) δ (ppm): 108.6, 110.1, 112.2, 114.1, 121.4, 122.4, 125.8, 127.3, 129.5, 135.1, 139.3, 141.2, 153.1, 166.0. LC/ESI-MS m/z: negative mode 286 ([M−H]$^−$), positive mode 288 ([M+H]$^+$).

Example 7

Preparation of
N-(3,4-dimethoxyphenyl)-1H-indazole-5-carboxamide

Yield 183 mg (61%) as a brownish solid, m.p. 258.3-261.3° C. $^1$H NMR (500 MHz, DMSO-d$_6$) δ (ppm): 3.74 (s, 3H, OMe), 3.76 (s, 3H, OMe), 6.93 (d, J=8.83 Hz, 1H), 7.36 (dd, J=2.53 и 8.83 Hz, 1H), 7.51 (d, J=2.52 Hz, 1H), 7.63 (td, J=0.94 и 8.83 Hz, 1H), 7.94 (dd, J=1.58 и 8.83 Hz, 1H), 8.24 (d, J=0.63 Hz, 1H), 8.46 (dd, J=0.63 и 1.58 Hz, 1H), 10.1 (s, 1H), 13.35 (s, 1H). $^{13}$C NMR (125 MHz, DMSO-d$_6$) δ (ppm): 55.6, 55.9, 105.8, 110.0, 112.2, 112.4, 121.1, 122.5, 125.7, 127.6, 133.2, 135.0, 141.1, 145.2, 148.6, 165.5. LC/ESI-MS m/z: negative mode 296 ([M−H]$^−$), positive mode 298 ([M+H]$^+$).

Example 8

Preparation of
N-(3,5-dichlorophenyl)-1H-indazole-5-carboxamide

Yield 190 mg (62%) as a white solid, m.p. 302.7-304.8° C. $^1$H NMR (500 MHz, DMSO-d$_6$) δ (ppm): 7.30 (t, J=1.89 Hz, 1H), 7.65 (d, J=8.51 Hz, 1H), 7.51 (d, J=2.52 Hz, 1H), 7.91 (dd, J=1.57 й 3.15 Hz, 1H), 7.92 (d, J=1.89 Hz, 1H), 8.28 (d, J=0.63 Hz, 1H), 8.48 (dd, J=0.63 й 1.58 Hz, 1H), 10.51 (s, 1H), 13.35 (s, 1H). $^{13}$C NMR (125 MHz, DMSO-d$_6$) δ (ppm): 110.1, 110.3, 118.3 (2×C), 121.7, 122.4, 122.7, 125.7, 126.6, 126.7, 134.1, 142.0, 145.2, 166.4. LC/ESI-MS m/z: negative mode 305 ([M−H]$^−$), positive mode 307 ([M+H]$^+$).

Example 9

Preparation of N-(3-chloro-4-fluorophenyl)-1H-indazole-5-carboxamide

Yield 156 mg (54%) as a white solid, m.p. 239.9-241.2° C. $^1$H NMR (500 MHz, DMSO-d$_6$) δ (ppm): 7.40 (t, J=9.15 Hz, 1H), 7.64 (d, J=8.82 Hz, 1H), 7.71-7.77 (m, 1H), 7.93 (dd, J=1.27/8.83 Hz, 1H), 8.11 (dd, J=2.53/6.94 Hz, 1H), 8.26 (s, 1H), 8.47 (s, 1H), 10.41 (s, 1H), 13.33 (s, 1H). $^{13}$C NMR (125 MHz, DMSO-d$_6$) δ (ppm): 110.2, 116.9 (d, J=21.7 Hz), 119.1 (d, J=18.2 Hz), 120.6 (d, J=6.73 Hz), 121.6 (d, J=32.4 Hz), 122.5, 125.7, 126.9, 135.1, 136.9, 141.3, 152.4, 154.3, 166.1. LC/ESI-MS m/z: negative mode 288 ([M−H]$^−$), positive mode 290 ([M+H]$^+$).

Example 10

Preparation of N-(4-chloro-3-fluorophenyl)-1H-indazole-5-carboxamide

Yield 95 mg (33%) as a white solid, m.p. 246.9-247.9° C. $^1$H NMR (500 MHz, DMSO-d$_6$) δ (ppm): 7.54 (t, J=8.52 Hz, 1H), 7.63 (dd, J=1.57/8.82 Hz, 1H), 7.65 (d, J=8.82 Hz, 1H), 7.93 (dd, J=1.58/8.51 Hz, 1H), 7.97 (dd, J=2.21/11.98 Hz, 1H), 8.27 (s, 1H), 8.47 (s, 1H), 10.52 (s, 1H), 13.34 (s, 1H). $^{13}$C NMR (125 MHz, DMSO-d$_6$) δ (ppm): 108.3 (d, J=25.7 Hz), 110.3, 113.1 (d, J=17.95 Hz), 117.1 (d, J=2.99 Hz), 121.6, 122.4, 125.7, 126.8, 130.5, 135.2, 140.2 (d, J=10.22 Hz), 156.1, 158.0, 166.3. LC/ESI-MS m/z: negative mode 288 ([M−H]$^−$), positive mode 290 ([M+H]$^+$).

Example 11

Preparation of
N-(3,4-difluorophenyl)-1H-indazole-5-carboxamide

Yield 163 mg (60%) as a white solid, m.p. 238.9-239.7° C. $^1$H NMR (500 MHz, DMSO-d$_6$) δ (ppm): 7.41 (q, J=9.14 Hz, 1H), 7.54-7.59 (m, 1H), 7.64 (d, J=8.45 Hz, 1H), 7.93 (dd, J=1.26/8.51 Hz, 1H), 7.96 (ddd, J=2.52/7.57/13.24 Hz, 1H), 8.78 (s, 1H), 8.47 (d, J=0.63 Hz, 1H), 10.42 (s, 1H), 13.33 (s, 1H). $^{13}$C NMR (125 MHz, DMSO-d$_6$) δ (ppm):

109.3 (d, J=21.7 Hz), 110.2, 116.6 (q, J=3.24 Hz), 117.4 (d, J=17.7 Hz), 121.5, 122.5, 125.7, 126.9, 135.1, 136.7 (dd, J=2.74/9.22 Hz), 141.2, 145.5 (dd, J=12.71/241.59 Hz), 149.0 (dd, J=13.22/242.85 Hz), 166.1. LC/ESI-MS m/z: negative mode 272 ([M−H]$^-$), positive mode 274 ([M+H]$^+$).

Example 12

Preparation of N-(5,6-dichloropyridin-3-yl)-1H-indazole-5-carboxamide

Yield 52 mg (17%) as a white solid, m.p. >290° C. (dec.). $^1$H NMR (500 MHz, DMSO-d$_6$) δ (ppm): 7.67 (d, J=8.82 Hz, 1H), 8.05 (d, J=8.51 Hz, 1H), 8.21 (s, 1H), 8.34 (s, 1H), 8.44 (s, 1H), 8.74 (s, 1H), 12.8 (s, 1H), 13.55 (s, 1H). $^{13}$C NMR (125 MHz, DMSO-d$_6$) δ (ppm): 110.1, 111.1, 120.5, 123.0, 123.2, 123.9, 126.3, 126.7, 127.1, 135.3, 136.1, 141.4, 163.1. LC/ESI-MS m/z: negative mode 306 ([M−H]$^-$), positive mode 309 ([M+H]$^+$).

Preparation of Tritium-Labeled Radioligand (Via a Methylation with Tritium-Labeled Methyl Methanesulfonate ([$^3$H]MMS)) (Method E).

To a solution of N-(3,4-dichlorophenyl)-1H-indazole-5-carboxamide (prepared as described in Example 1/Method C, 75.0 mg, 0.25 mmol) in N,N-dimethylformamide (DMF, 2.0 mL; extra dry over molecular sieves, 99.8%, Acros) and potassium carbonate (43.0 mg, 0.31 mmol) was added methyl methanesulfonate (MMS, 45.0 mg, 0.41 mmol; Aldrich, 99%). The solution was stirred at room temperature for 24 hours (TLC-control: dichloromethane/methanol, 9:1, v/v), hydrolyzed with water (20 mL), acidified with diluted hydrochloric acid (2N, 0.5 mL), and sonicated for 5 min. The yellowish precipitate was filtered under reduced pressure, washed with water (3×5 mL) and dried at 70° C. The isomeric mixture, containing N1-methylated regioisomer product of Example 13 and N2-methylated regioisomer product of Example 14 (LC/ESI-MS ratio N1/N2-methyl isomer, 1.65:1), was separated by column chromatography to silica gel (eluent: dichloromethane/methanol, 9:1, v/v). The compound of Example 13 was additionally purified by RP-HPLC (MeOH/H$_2$O, 75:25).

Example 13

Preparation N1-methylated isomer N-(3,4-dichlorophenyl)-1-methyl-1H-indazole-5-carboxamide (NTZ091)

Yield 37 mg (47%) as a white solid, R$_f$=0.80 (eluent: dichloromethane/methanol, 9:1, v/v), m.p. 193.2-194.3° C. $^1$H NMR (500 MHz, DMSO-d$_6$) δ (ppm): 4.09 (s, 3H, N1Me), 7.61 (d, J=8.82 Hz, 1H), 7.76 (d, J=8.20 Hz, 1H), 7.78 (dd, J=2.21/8.83 Hz, 1H), 7.98 (dd, J=1.57/8.82 Hz, 1H), 8.18 (d, J=2.52 Hz, 1H), 8.24 (d, J=0.63 Hz, 1H), 8.46 (dd, J=0.63/1.57 Hz, 1H), 10.49 (s, 1H). $^{13}$C NMR (125 MHz, DMSO-d$_6$) δ (ppm): 35.7 (N1Me), 109.8, 120.3, 121.5, 121.9, 123.1, 125.0, 125.6, 126.7, 130.7, 131.0, 134.2, 139.7, 140.9, 166.1. LC/ESI-MS m/z: negative mode 318.05 ([M−H]$^-$), positive mode 320.14 ([M+H]$^+$). Purity (LC/ESI-MS, UV$_{max}$ 236 nm): 99.55% (neutral pH), reaction time: 9.32 min.

Analytical RP-HPLC conditions:

The analytic sample was dissolved in methanol (1.0 mg/mL) and 8.0 μL were injected. A linear mobile phase gradient was used mobile phase A as 100% H$_2$O 2.0 mM ammonium acetate, and mobile phase B as 100% methanol 2.0 mM ammonium acetate. The gradient starts directly from 60% A and 40% B to 100% B in 10 min. Afterwards, rising with 100% B for 10 min and 0% A. A NUCLEODUR C18 Gravity (EC 50/2, 3.0 μm particle size, flowrate 0.3 mL/min) analytical column from Macherey & Nagel (Düren, Germany) with a pump device Agilent 1100 binary pump from Agilent Technoligies (Böblingen, Germany) were used. The purity of the compound was detested by HPLC-UV obtained on LC/MS instrument (Applied Biosystems API 2000 LC-MS/MS, HPLC Agilent 1110) using a diode array detector (DAD) with an UV absorption from 220 to 400 nm.

Preparative RP-HPLC Conditions:

The preparative sample (37.0 mg) was dissolved in 9.0 mL MeOH/H$_2$O (7:2) and max 4.0 mL of the sample were injected. The gradient remains isocratic (MeOH (Sol. B)/H$_2$O (Sol. A), 75:25) for 20 min. An Eurospher 100-10 C18 column (250×20 mm, 10 μm particle size, flowrate 20.0 mL/min) from Knauer (Berlin, Germany) and a preparative pump 1800 from Knauer Smartline with an UV detection in the range from 220 to 400 nm (UV$_{max}$ 243 nm) were used.

The physicochemical properties of Example 13 are shown in Table 1:

TABLE 1

| | |
|---|---|
| State (20.0° C.): | Solid |
| Colour: | white, colorless crystals after rectystallization from MeOH |
| Melting point range (° C.): | 193.2-194.3 |
| Solubilty inorganic solvents: | Soluble (0.01-0.03 mL per 1.0 mg) in DMSO, DMF, MeOH, EtOH, i-PrOH, n-BuOH, t-BuOH, acetonitrile. Very slightly soluble (1.0-10.0 mL per 1.0 mg) in dichloromethane and ethyl acetate Insoluble (>10 mL per 1.0 mg) in petroleum ether, Et$_2$O and n-hexane |
| Solubility in water (μg/mL): | <0.01 (at 22.5° C., pH 7.4, pH 1.0-2.0) <0.035 (at 90° C., pH 7.4, pH 1.0) Very slightly soluble in hot water |
| Stability: | Stable under specified storage temperature (room temperature) |

Example 14

Preparation of N2-methylated isomer N-(3,4-dichlorophenyl)-2-methyl-2H-indazole-5-carboxamide Yield 7.2 mg (9%) as a white solid, R$_f$=0.57 (eluent: dichloromethane/methanol, 9:1, v/v), m.p. 180.7-181.6° C.; $^1$H NMR (500 MHz, DMSO-d$_6$) δ (ppm): 4.23 (s, 3H, N2Me), 7.60 (d, J=8.82 Hz, 1H), 7.68 (dt, J=8.82/0.95 Hz, 1H), 7.75 (s, 1H), 7.76 (dd, J=2.21/8.83 Hz, 1H), 8.16 (d, J=0.63 Hz, 1H), 8.44 (dd, J=0.94/1.89 Hz, 1H), 8.58 (s, 1H), 10.44 (s, 1H). $^{13}$C NMR (125 MHz, DMSO-d$_6$) δ (ppm): 48.8 (N2Me), 116.9, 120.4, 120.9, 121.5, 122.4, 124.6, 125.0, 127.1, 127.2, 130.7, 131.0, 139.8, 149.1, 166.4; LC/ESI-MS m/z: negative mode 318.05 [M−H]$^-$, positive mode 320.14 [M+H]$^+$.

The compounds represented in Example 13 and Example 14 can be used in mixtures or independently from each other as biologically active ingredients in pharmaceutical preparations.

Example 15

Preparation of biologically active mixture (4.7:1) of the compounds from Example 13 and Example 14: N1-methyl isomer N-(3,4-dichlorophenyl)-1-methyl-1H-indazole-5-carboxamide (Example 13) and N2-methyl isomer N-(3,4-dichlorophenyl)-2-methyl-2H-indazole-5-carboxamide (Example 14). The mixture was prepared in an analogous manner to that in Example 13 without further purification. The crude product mixture (N1-/N2-methyl: 4.7:1) was recrystallized from MeOH. Yield 62 mg (79%) as a white solid, LC/ESI-MS m/z: 320.14 [M+H]$^+$; 318.05 [M−H]$^-$.

Purity (LC/ESI-MS, UV 208-294 nm): 95.5% (neutral pH), reaction time: 8.85 (N2-methyl)/9.32 (N1-methyl) min.

Example 16

Preparation of N-(3,4-dichlorophenyl)-1-methyl-1H-indole-5-carboxamide

This compound was prepared according to the same procedure of Examples 13 and 14 by using N-(3,4-dichlorophenyl)-1H-indole-5-carboxamide as a starting material (obtained in Example 2). Yield 17 mg (68%) as a white solid, m.p. 178.9-180.3° C. $^1$H NMR (500 MHz, DMSO-$d_6$) δ (ppm): 3.83 (s, 3H, N1Me), 6.59 (dd, J=0.95/3.16 Hz, 1H), 7.44 (d, J=3.16 Hz, 1H), 7.55 (d, J=8.83 Hz, 1H), 7.59 (d, J=8.82 Hz, 1H), 7.78 (dd, J=2.52/3.15 Hz, 1H), 7.80 (dd, J=2.52/3.47 Hz, 1H), 8.20 (d, J=2.21 Hz, 1H), 8.26 (d, J=1.26 Hz, 1H), 10.35 (s, 1H). $^{13}$C NMR (125 MHz, DMSO-$d_6$) δ (ppm): 32.8, 101.9, 109.7, 120.2, 121.1 (2×C), 121.4, 124.7, 125.2, 127.5, 130.6, 130.9, 131.5, 138.3, 140.0, 166.9. LC/ESI-MS m/z: negative mode 318 ([M−H]$^-$), positive mode 320 ([M+H]$^+$).

Example 17

Preparation of N1-methylated isomer N-(3-chloro-4-fluorophenyl)-1-methyl-1H-indazole-5-carboxamide This compound was prepared according to the same procedure of Examples 13 and 14 by using N-(3-chloro-4-fluorophenyl)-1H-indazole-5-carboxamide as a starting material (obtained in Example 9). The isomeric mixture, containing N1-methylated regioisomer product of Example 17 and N2-methylated regioisomer product of Example 18 (LC/ESI-MS ratio N1/N2-methyl isomer, 1.9:1), was separated using the preparative RP-HPLC conditions as described above in Example 13 (MeOH/H$_2$O, 70:30). Yield 35 mg (52%) as a white solid, $R_f$=0.74 (eluent: dichloromethane/methanol, 9:1, v/v), m.p. 171.4-172.4° C. $^1$H NMR (500 MHz, DMSO-$d_6$) δ (ppm): 4.09 (s, 3H, N1Me), 7.41 (t, J=9.14 Hz, 1H), 7.74 (ddd, J=2.83/4.41 å 8.82 Hz, 1H), 7.76 (d, J=8.83 Hz, 1H), 7.98 (dd, J=1.89 å 8.83 Hz, 1H), 8.10 (dd, J=2.52/6.94 Hz, 1H), 8.24 (d, J=0.95 Hz, 1H), 8.46 (q, J=0.94 Hz, 1H), 10.42 (s, 1H). $^{13}$C NMR (125 MHz, DMSO-$d_6$) δ (ppm): 35.7 (N1Me), 109.8, 116.9 (d, J=21.6 Hz), 119.1 (d, J=18.2 Hz), 120.7 (d, J=6.73 Hz), 121.8 (d, J=4.49 Hz), 123.1, 125.6, 126.9, 134.1, 136.8 (d, J=2.99 Hz), 140.9, 152.4, 154.3, 165.9. LC/ESI-MS m/z: negative mode 302 ([M−H]$^-$), positive mode 304 ([M+H]$^+$). Purity (LC/ESI-MS, UV$_{max}$ 234 nm): 99.45% (neutral pH), reaction time: 8.25 min.

Example 18

Preparation of N2-methylated isomer N-(3-chloro-4-fluorophenyl)-2-methyl-2H-indazole-5-carboxamide Yield 13 mg (20%) as a white solid, $R_f$=0.56 (eluent: dichloromethane/methanol, 9:1, v/v), m.p. 187.8-188.1° C. $^1$H NMR (500 MHz, DMSO-$d_6$) δ (ppm): 4.21 (s, 3H, N2Me), 7.40 (t, J=9.14 Hz, 1H), 7.68 (td, J=0.94/9.14 Hz, 1H), 7.74 (ddd, J=2.84/4.41 å 9.14 Hz, 1H), 7.77 (dd, J=1.89/9.14 Hz, 1H), 8.10 (dd, J=2.52/6.93 Hz, 1H), 8.44 (q, J=0.95 Hz, 1H), 8.59 (s, 1H), 10.37 (s, 1H). $^{13}$C NMR (125 MHz, DMSO-$d_6$) δ (ppm): 40.4 (N2Me), 116.8, 116.9 (d, J=21.7 Hz), 119.1 (d, J=18.2 Hz), 120.6 (d, J=6.98 Hz), 120.9 121.7, 122.2, 124.5, 127.1 (d, J=18.7 Hz), 136.9 (d, J=2.99 Hz), 149.0, 152.4, 154.3, 166.2. LC/ESI-MS m/z: negative mode 302 ([M−H]$^-$), positive mode 304 ([M+H]$^+$).

Example 19

Preparation of N1-methylated isomer N-(3,4-difluorophenyl)-1-methyl-1H-indazole-5-carboxamide This compound was prepared according to the same procedure of Examples 13 and 14 by using N-(3,4-difluorophenyl)-1H-indazole-5-carboxamide as a starting material (obtained in Example 11). The isomeric mixture, containing N1-methylated regioisomer product of Example 19 and N2-methylated regioisomer product of Example 20 (LC/ESI-MS ratio N1/N2-methyl isomer, 2.8:1), was separated using the preparative RP-HPLC conditions as described above in Example 13 (MeOH/H$_2$O, 60:40). Yield 18.4 mg (27%) as a white solid, $R_f$=0.77 (eluent: dichloromethane/methanol, 9:1, v/v), m.p. 172.4-172.6° C. $^1$H NMR (500 MHz, DMSO-$d_6$) δ (ppm): 4.09 (s, 3H, N1Me), 7.41 (q, J=10.72 Hz, 1H), 7.54-7.59 (m, 1H), 7.75 (d, J=8.83 Hz, 1H), 7.95 (dd, J=2.52/7.57 Hz, 1H), 7.98 (dd, J=1.58/8.83 Hz, 1H), 8.24 (d, J=0.63 Hz, 1H), 8.45 (q, J=0.95 Hz, 1H), 10.43 (s, 1H). $^{13}$C NMR (125 MHz, DMSO-$d_6$) δ (ppm): 35.7 (N1Me), 109.3 (d, J=21.7 Hz), 109.8, 116.6 (q, J=3.24 Hz), 117.4 (d, J=17.7 Hz), 121.7, 123.1, 125.6, 126.9, 134.1, 136.6 (dd, J=2.74/9.22 Hz), 140.9, 145.5 (dd, J=12.47/241.35 Hz), 149.0 (dd, J=12.96 å 242.84 Hz), 165.9. LC/ESI-MS m/z: negative mode 286 ([M−H]$^-$), positive mode 288 ([M+H]$^+$). Purity (LC/ESI-MS, UV$_{max}$ 236 nm): 99.58% (neutral pH), reaction time: 7.52 min.

Example 20

Preparation of N2-methylated isomer N-(3,4-difluorophenyl)-2-methyl-2H-indazole-5-carboxamide Yield 7.0 mg (10%) as a white solid, $R_f$=0.65 (eluent: dichloromethane/methanol, 9:1, v/v), m.p. 187.8-188.1° C. $^1$H NMR (500 MHz, DMSO-$d_6$) δ (ppm): 4.21 (s, 3H, N2Me), 7.41 (qd, J=10.4/10.72 Hz, 1H), 7.54-7.59 (m, 1H), 7.68 (dt, J=9.14/0.95 Hz, 1H), 7.77 (dd, J=1.57/9.14 Hz, 1H), 7.95 (ddd, J=2.53/7.57 å 13.25 Hz, 1H), 8.43 (q, J=0.63 Hz, 1H), 8.59 (s, 1H), 10.39 (s, 1H). $^{13}$C NMR (125 MHz, DMSO-$d_6$) δ (ppm): 39.2 (N2Me), 109.2 (d, J=21.7 Hz), 110.2, 116.6 (q, J=3.24 Hz), 116.8, 117.4 (d, J=17.7 Hz), 120.9, 122.1, 124.5, 127.1 (d, J=24.7 Hz), 135.1, 136.7 (dd, J=2.74 å 9.22 Hz), 145.5 (dd, J=12.46 å 241.59 Hz), 149.0 (dd, J=13.21 å 242.84 Hz), 166.2. LC/ESI-MS m/z: negative mode 286 ([M−H]$^-$), positive mode 288 ([M+H]$^+$).

Example 21

N-(3,4-dichlorophenyl)-1-(2-methoxyethyl)-1H-indazole-5-carboxamide

This compound was prepared according to the same procedure of Examples 13 and 14 by using N-(3,4-dichlorophenyl)-1H-indazole-5-carboxamide as a starting material (obtained in Example 2) and 2-bromoethyl methyl ether as an alkylating reagent. The crude product was purified by column chromatography on silica gel (eluent: dichloromethane/methanol, 9:1, v/v). Yield 35 mg (22%) as a white solid, m.p. 116.8-117.8° C. $^1$H NMR (500 MHz, DMSO-$d_6$) δ

(ppm): 3.18 (s, 3H, Me), 3.77 (t, J=5.36 Hz, 2H), 4.61 (t, J=5.04 Hz, 2H), 7.61 (d, J=8.82 Hz, 1H), 7.79 (ddd, J=3.47/5.68/8.83 Hz, 2H), 7.95 (d, J=1.58/8.83 Hz, 1H), 8.18 (d, J=2.21 Hz, 1H), 8.28 (s, 1H), 8.46 (s, 1H), 10.46 (s, 1H). $^{13}$C NMR (125 MHz, DMSO-$d_6$) δ (ppm): 48.4, 58.2, 70.7, 110.1, 120.3, 121.5, 121.8, 123.1, 125.0, 125.6, 126.8, 130.6, 131.0, 134.6, 139.7, 141.2, 166.1. LC/ESI-MS m/z: negative mode 363 ([M−H]$^−$), positive mode 365 ([M+H]$^+$).

Example 22

Preparation of (E)-N-((1H-indazol-5-yl)methylene)-3,4-dichloroaniline

Method D

A solution of 1H-indazole-5-carboxaldehyde (146 mg, 1.0 mmol), 3,4-dichloroaniline (162 mg, 1.0 mmol) and acetic acid (0.2 mL, 0.1 mmol) in ethanol (3 mL) was stirred under reflux for 30 min during which time a precipitation took place. After cooling to room temperature, water (30 mL) was added and the reaction mixture was sonificated for 5 min. The precipitate formed was filtered, dried at 70° C. and purified by column chromatography on silica gel (eluent: dichloromethane/methanol, 9:1, v/v) to afford 257 mg (89%) of the product as a white solid, m.p. 207.1-207.5° C. $^1$H NMR (500 MHz, DMSO-$d_6$) δ (ppm): 7.27 (dd, J=2.52/8.51 Hz, 1H), 7.55 (d, J=2.53 Hz, 1H), 7.63 (s, 1H), 7.65 (s, 1H), 8.12 (dd, J=1.26/8.83 Hz, 1H), 8.24 (s, 1H), 8.29 (s, 1H), 8.73 (s, 1H), 13.35 (s, 1H). $^{13}$C NMR (125 MHz, DMSO-$d_6$) δ (ppm): 110.9, 122.1, 122.7, 123.0, 125.1, 125.2, 127.7, 128.9, 131.1, 131.7, 135.2, 141.5, 151.9, 163.2. LC/ESI-MS m/z: negative mode 289 ([M−H]$^−$), positive mode 291 ([M+H]$^+$).

The compounds of the following Examples 23-26 were obtained according to the same procedure described in Example 22/Method D above by a reaction of the corresponding 1H-indazole-5-carboxaldehyde or 1-methyl-1H-indazole-5-carboxaldehyde with the appropriate aniline or aminopyridine.

Example 23

Preparation of (E)-N-((1H-indazol-5-yl)methylene)-4-chloro-3-fluoroaniline

Yield 158 mg (58%) as a white solid, m.p. 198.7-199.2° C. $^1$H NMR (500 MHz, DMSO-$d_6$) δ (ppm): 7.15 (ddd, J=1.26/2.52 å 8.51 Hz, 1H), 7.37 (dd, J=2.2 å 10.72 Hz, 1H), 7.59 (t, J=8.52 Hz, 1H), 7.64 (d, J=8.83 Hz, 1H), 8.02 (dd, J=1.26 å 8.83 Hz, 1H), 8.24 (s, 1H), 8.28 (s, 1H), 8.73 (s, 1H), 13.35 (s, 1H). $^{13}$C NMR (125 MHz, DMSO-$d_6$) δ (ppm): 109.4 (d, J=21.45 Hz), 110.9, 116.1 (d, J=17.95 Hz), 119.0 (d, J=2.74 Hz), 123.0, 125.1 (d, J=8.33 Hz), 128.8, 130.9, 135.2, 141.5, 152.6 (d, J=7.97 Hz), 156.7, 158.6, 163.1. LC/ESI-MS m/z: negative mode 272 ([M−H]$^−$), positive mode 274 ([M+H]$^+$).

Example 24

Preparation of (E)-N-((1H-indazol-5-yl)methylene)-3-chloro-4-fluoroaniline

Yield 107 mg (39%) as a white solid, m.p. 171.9-172.6° C. $^1$H NMR (500 MHz, DMSO-$d_6$) δ (ppm): 7.29 (ddd, J=2.52/4.41 and 8.83 Hz, 1H), 7.44 (t, J=8.83 Hz, 1H), 7.52 (dd, J=2.52/6.62 Hz, 1H), 7.64 (d, J=8.83 Hz, 1H), 8.02 (dd, J=1.26/8.83 Hz, 1H), 8.23 (s, 1H), 8.27 (s, 1H), 8.72 (s, 1H), 13.35 (s, 1H). $^{13}$C NMR (125 MHz, DMSO-$d_6$) δ (ppm): 110.9, 117.3 (d, J=21.69 Hz), 120.0 (d, J=18.7 Hz), 122.2 (d, J=7.23 Hz), 122.5, 123.0, 125.0 (d, J=19.94 Hz), 128.9, 135.2, 141.4, 149.0 (d, J=3.24 Hz), 154.4, 156.4, 162.6. LC/ESI-MS m/z: negative mode 272 ([M−H]$^−$), positive mode 274 ([M+H]$^+$).

Example 25

Preparation of (E)-N-((1H-indazol-5-yl)methylene)-5,6-dichloropyridin-3-amine

Yield 52 mg (29%) as a yellow solid, m.p. 236.9-238.4° C. $^1$H NMR (500 MHz, DMSO-$d_6$) δ (ppm): 7.65 (d, J=8.51 Hz, 1H), 8.02 (dd, J=1.26/8.83 Hz, 1H), 8.14 (dd, J=2.20 Hz, 1H), 8.26 (s, 1H), 8.30 (s, 1H), 8.35 (d, J=2.52 Hz, 1H), 8.82 (s, 1H), 13.37 (s, 1H). $^{13}$C NMR (125 MHz, DMSO-$d_6$) δ (ppm): 111.0, 123.0, 125.1, 125.6, 128.6, 129.3, 130.9, 135.4, 141.6, 141.8, 143.6, 148.1, 165.4. LC/ESI-MS m/z: negative mode 290 ([M−H]$^−$), positive mode 292 ([M+H]$^+$).

Preparation of (E)-N-((1H-indazol-5-yl)methylene)-5,6-dichlopyridin-3-amine trifluoroacetic acid The compound prepared in Example 25 (73.9 mg, 0.25 mmol) was dissolved in neat trifluoroacetic acid (TFA, 3.0 mL) and the mixture was stirred at room temperature overnight. The excess of acid was evaporated and the traces of TFA were removed by a co-evaporation with toluene (2×10 mL). The residue was dried at 70° C. to afford 79 mg (77%) of a yellow solid, m.p. 221.2-223.6° C. $^1$H NMR (500 MHz, DMSO-$d_6$) δ (ppm): 5.51 (s, 2H), 7.65 (d, J=8.51 Hz, 1H), 7.82 (d, J=1.26 Hz, 1H), 8.14 (dd, J=2.20 Hz, 1H), 8.26 (s, 1H), 8.30 (s, 1H), 8.44 (d, J=0.63 Hz, 1H), 10.01 (s, 1H), 13.45 (s, 1H). $^{13}$C NMR (125 MHz, DMSO-$d_6$) δ (ppm): 111.2, 122.4, 122.9 (d), 124.6, 125.4 (d), 127.6, 129.4, 130.9, 133.9, 141.6, 141.8, 146.0, 148.1, 165.4, 192.4.

Example 26

Preparation of (E)-3,4-dichloro-N-((1-methyl-1H-indazole-5-yl)methylene)aniline

Yield 274 mg (90%) as a yellowish solid 145.7-146.2° C. $^1$H NMR (500 MHz, DMSO-$d_6$) δ (ppm): 74.09 (s, 3H, N1Me), 7.28 (dd, J=2.53/8.52 Hz, 1H), 7.56 (d, J=2.53 Hz, 1H), 7.63 (s, 1H), 7.65 (s, 1H), 7.75 (dd, J=0.63/8.83 Hz, 1H), 8.05 (dd, J=1.58/8.83 Hz, 1H), 8.22 (d, J=0.94 Hz, 1H), 8.28 (s, 1H), 8.74 (s, 1H). $^{13}$C NMR (125 MHz, DMSO-$d_6$) δ (ppm): 35.7, 110.5, 122.1, 122.7, 123.6, 125.0, 125.3, 125.2, 127.8, 128.9, 131.1, 131.7, 134.2, 141.1, 151.8, 163.0. LC/ESI-MS m/z: negative mode 303 ([M−H]$^−$), positive mode 305 ([M+H]$^+$).

In Table 2 are presented the compounds of Examples 1-26 obtained according to the general procedures A to E of the present invention. Their structures, methods for their preparation, yields and melting points are reported.

TABLE 2

| EXAMPLE | Method | Yield (%) | M. p. |
|---|---|---|---|
| 1 (1H-indazole-5-carboxamide with N-(3,4-dichlorophenyl)) | A<br>B<br>C | 30<br>23<br>67 | 397.2 |
| 2 (1H-indole-5-carboxamide with N-(3,4-dichlorophenyl)) | C | 17 | 305.2 |
| 3 (1H-indazole-5-carboxamide with N-(3-chloro-4-methoxyphenyl)) | A | 11 | 301.7 |
| 4 (1H-indazole-5-carboxamide with N-(4-chloro-3-methoxyphenyl)) | A | 11 | 301.7 |
| 5 (1H-indazole-5-carboxamide with N-(3-chloro-4-hydroxyphenyl)) | C | 59 | 287.7 |
| 6 (1H-indazole-5-carboxamide with N-(4-chloro-3-hydroxyphenyl)) | C | 53 | 287.7 |

TABLE 2-continued
| EXAMPLE | Method | Yield (%) | M. p. |
|---|---|---|---|
| 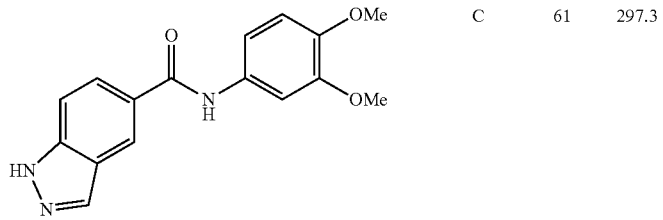<br>7 | C | 61 | 297.3 |
| 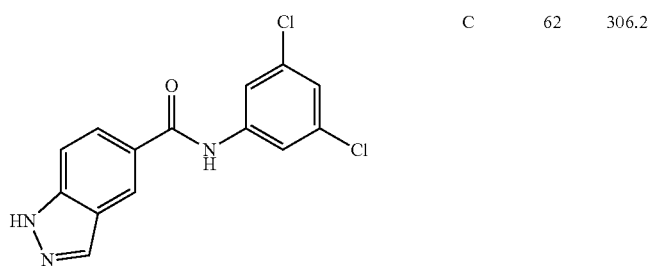<br>8 | C | 62 | 306.2 |
| 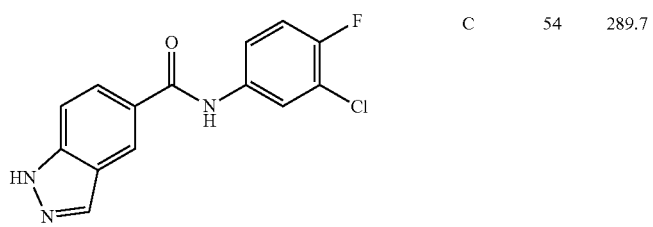<br>9 | C | 54 | 289.7 |
| 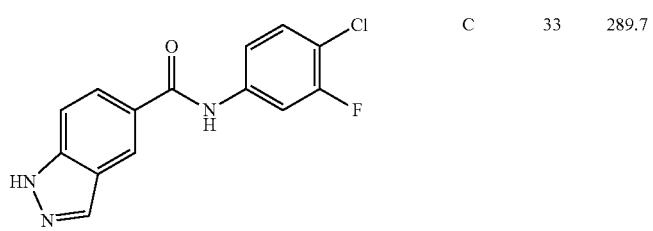<br>10 | C | 33 | 289.7 |
| 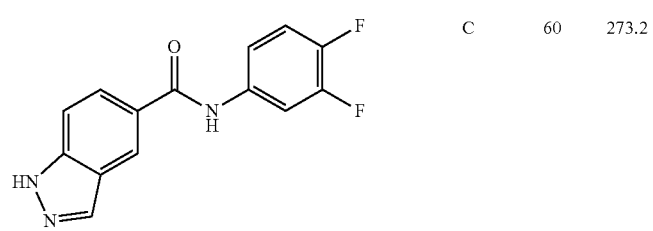<br>11 | C | 60 | 273.2 |

TABLE 2-continued

| EXAMPLE | Method | Yield (%) | M. p. |
|---|---|---|---|
| 12 (1H-indazole-5-carboxamide with 5,6-dichloropyridin-3-yl) | C | 18 | 307.1 |
| 13 (1-methyl-1H-indazole-5-carboxamide with 3,4-dichlorophenyl) | E | 47 | 320.2 |
| 14 (2-methyl-2H-indazole-5-carboxamide with 3,4-dichlorophenyl) | E | 9 | 320.2 |
| 15 (in mixture, 13/14 = 4.7:1) | E | 79 | 320.2 |
| 16 (1-methyl-1H-indole-5-carboxamide with 3,4-dichlorophenyl) | E | 68 | 319.2 |
| 17 (1-methyl-1H-indole-5-carboxamide with 3-chloro-4-fluorophenyl) | E | 52 | 303.7 |

TABLE 2-continued

| EXAMPLE | Method | Yield (%) | M. p. |
|---|---|---|---|
| 18 | E | 20 | 303.7 |
| 19 | E | 27 | 287.3 |
| 20 | E | 10 | 287.3 |
| 21 | E | 22 | 364.2 |
| 22 | D | 89 | 290.2 |

TABLE 2-continued

| EXAMPLE | Method | Yield (%) | M. p. |
|---|---|---|---|
| 23 | D | 58 | 273.7 |
| 24 | D | 39 | 273.7 |
| 25 | D | 29 | 291.1 |
| 26 | D | 90 | 304.2 |

Example 27

The Pharmacological Activity of the Compounds of Formula I was Tested Using the Following Biological Experiments In Vitro MAO-A and MAO-B Enzyme Activities Assay The MAO-A and MAO-B enzymatic activity of the compounds was measured in 96-well-plates using a continuous fluorescence-based assay. This assay was adapted from the method described by Holt et al. (*Anal. Biochem.*, 244, 384-392, 1997). The MAO experiments were performed using commercial assay kit (Amplex® Red, Invitrogen A12214). The kit was stored frozen at ≤−20° C. and protected from light before use. The Amplex® Red MAO assay kit was used for the detection of $H_2O_2$ released from the biological sample. Subsequently, a reaction of 10-acetyl-3,7-dihydroxyphenoxazine (ADHP, Amplex® Red reagent) with $H_2O_2$ in the presence of a peroxidase (horse-radish peroxidase-coupled reaction, HRP) led to the production of resofurin. The production of $H_2O_2$ and consequently of resofurine which was determined using a fluorescence microplate reader for the continuous measurement of amine oxidase activity (Holt et al., *Anal. Biochem.*, 244, 384-392, 1997). To ensure an optimal efficiency of the Amplex® Red reagent, the MAO assay's were performed as recommended by the manufacturer (at pH 7-8) using the included reaction buffer.

Membrane Preparation of Rat Liver Mitochondria

Male Sprague-Dawley (Harlan Sprague Dawley, Dublin, Va., US) rats (250-300 g) were sacrificed under light anesthesia and their livers were dissected. After that, 10.0 g of liver were sliced in 15.0 mL of an ice cold 5.0 mM Hepes buffer (pH 7.4) containing 210 mM mannitol, 70 mM sucrose, 0.5 mM ethyleneglycoltetraacetic acid (EGTA) and 2.0 mg/mL of bovine serum albumin (BSA) and homogenized using a glass/teflon potter (10 ups and downs at 1100 rpm). After homogenization, the volume is adjusted to 100 mL with the same buffer. After a low speed centrifugation (10 min at 600 g; 4° C.), the supernatant is further centrifuged at 15,000 rpm for 5 min at +4° C. The resulting pellet was resuspended in 2.0 mL of a 50 mM sodium/phosphate buffer (pH 7.4) and stored at −80° C. in aliquots of 1.0 mL each until further use.

Rat MAO-A Assay

Assays were performed in 96 well-plates in a final volume of 200 µL at room temperature. Rat liver mitochondria were pre-treated for 15 min at room temperature with an aqueous solution of deprenyl (30 nM) to irreversibly inhibit MAO-B activity. The test compound (2.0 µL) was dissolved in DMSO (100%), added to 90.0 µL of mitochondria (25.0 µg prot) and incubated for 30 min prior to the addition of 90 µL of freshly prepared Amplex® Red reagent. The Amplex® Red reagent was prepared as recommended in the kit from Invitrogen (A12214). For each 96-well-plate, 1.0 mg of Amplex® Red, dissolved in 200 µL of DMSO (100%) and 100 µL of reconstituted horse-radish peroxidase (HRP 200 U/mL, Sigma Aldrich P6782) stock solution (kit vial+1.0 mL of sodium/phosphate buffer) were added to 9700 µL of sodium phosphate buffer (250 mM at pH 7.4). Enzymatic reaction was started by the addition of 20 µL/well of an aqueous solution (300 µM final concentration) of the substrate p-tyramine (Alfa Aesar A12220). Fluorescence measurements were performed for 45 min using a microplate fluorescence reader (Polarstar BMG Labtech, Germany) with excitation at 544 nm and emission at 590 nm. Clorgyline (1.0 µM) from Sigma Aldrich (M3778) was used to determine non-MAO-A enzyme activity and concentration-response curves of clorgyline serve as positive control.

Rat MAO-B Assay

Assays are performed as described for MAO-A except that mitochondria was pre-treated with clorgyline (30 nM) to irreversibly inhibit MAO-A activity. 5.0 µg prot/assay were used instead of 25.0 µg for MAO-A. Non-MAO-B enzyme activity was determined in the presence of deprenyl (1.0 µM) and concentration-response curves of deprenyl serve as positive control.

Human MAO-A Assay

The recombinant human MAO-A enzyme was expressed in baculovirus-infected insected cells purchased from Sigma-Aldrich (M7316). The assay was carried out in 96 well-plates in a final volume of 200 µL at room temperature. According to the experiment protocol, a solution of test compound (2.0 µL) in DMSO (100%) was added to 90.0 µL of protein solution (0.3 µg prot/well, containing 6.6 µL protein and 9.993 µL phosphate buffer) and incubated for 30 min prior to the addition of 90 µL of freshly prepared Amplex® Red reagent. The Amplex® Red reagent was prepared as described for rat MAO-A. The enzymatic reaction was started by the addition of substrate p-tyramine (20.0 µL) prepared from 45 µL p-tyramine hydrochloride in water (100 mM) and 2955 µL phosphate buffer (150 µM final concentration of tyramine). Fluorescence measurements were performed for 45 min using a microplate fluorescence reader (Polarstar BMG Labtech, Germany) with excitation at 544 nm and emission at 590 nm. Concentration-response curves of clorgyline (2.0 µL) serve as positive control. DMSO (2.0 µL) was used as negative control.

Human MAO-B Assay

The recombinant human MAO-B enzyme was expressed in baculovirus-infected insected cells purchased from Sigma-Aldrich (M7441). The assays were performed as described for human MAO-A except that Selegeline (2.0 µL) was used as positive control for MAO-B activity. 90.0 µL protein suspension for MAO-B contains 20.0 µL protein and 9,980 mL buffer (0.9 µg prot/well).

MAO-B Reactivation Experiment

To investigate whether the compounds of formula I are reversible or irreversible MAO-B inhibitors, the inhibition of the enzymatic activity was detected for two of compounds N-(3,4-dichlorophenyl)-1H-indazole-5-carboxamide and N-(3,4-dichlorophenyl)-1-methyl-1H-indazole-5-carboxamide using the experimental protocol described below. The time-dependent inhibition studies were performed using human MAO-B and the tested compounds deduced at their corresponding $IC_{80}$ values versus p-tyramine (estimated at 150 µM final concentration) in the test samples with and without enzyme inhibitor. The enzymatic activity of the test compounds was measured for 22 min in the presence of low substrate concentration of 10 µM following by a gradually increasing of the substrate concentration to 1.0 mM final concentration of p-tyramine. A reactivation of MAO-B activity was observed after increasing of the substrate concentration. The enzyme reactivation was monitored by a fluorescence measurement over a period of 5 hours. At this final substrate concentration such as reversible inhibitors can be replaced by the competing substrate. In the case of the test compounds of formula I, an elevated fluorescence can be detected, indicating that the test compounds are reversible MAO-B inhibitors. The same result was observed for the reference compound safinamide (Maj et al., *Eur. J. Pharmacol.*, 359, 27-32, 1998; Marzo et al., *Pharmacol. Res.*, 50, 77-85, 2004) which was used as a reversible inhibitor. Selegiline (Youdim et al., *Br. J. Pharmacol.*, 132, 500-506, 2001) was used as an irreversible inhibitor.

Figure 5:
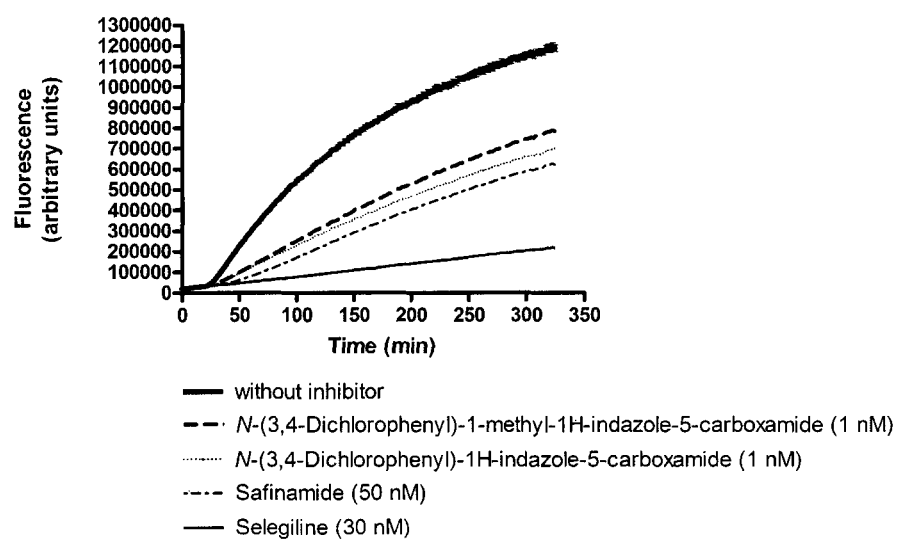
FIG. 5 shows the results of the time-dependent inhibition (experiment for investigation of reversible inhibition) of human recombinant MAO-B of N-(3,4-dichlorophenyl)-1H-indazole-5-carboxamide and N-(3,4-dichlorophenyl)-1-methyl-1H-indazole-5-carboxamide (each at the concentration that represents its $IC_{80}$ value) in the presence of the substrate p-tyramine versus irreversible (selegiline 30 nM), reversible (safinamide 50 nM) inhibitor and without inhibitor.

The results of the reversibility experiments are illustrated in FIG. 5.

Assay for Mode of MAO-B Inhibition

To evaluate the mode of MAO-B inhibition for the compounds of formula I, the representative inhibitor N-(3,4-dichlorophenyl)-1-methyl-1H-indazole-5-carboxamide (Example 13) was examined in substrata-dependent kinetic experiments. The type of MAO-B enzyme inhibition was determined by Michaelis-Menten kinetic experiments and sets of Lineweaver-Burk plots were generated. The reciprocal MAO-B activity was plotted against the reciprocal substrate concentration (n=2). The initial catalytic rates of human MAO-B were measured at six different concentrations of the substrate p-tyramine (0.05, 0.1, 0.25, 0.5, 1.0 and 1.5 mM) in the absence and in the presence of six different concentration of the inhibitor (0.1, 0.2, 0.5, 1.0, 5.0 and 10 nM). The enzymatic reactions and measurements were performed using human MAO-B assay conditions, applied for the determination of $IC_{50}$ values. The experiment was performed in duplicate. The Lineweaver-Burks plot for the compound in Example 13 are linear and intersected at the y-axis with the plot for the uninhibited enzyme. The results of the reversibility experiments and the assays of the mode of inhibition suggested that the compounds of formula I are reversible and competitive MAO-B inhibitors.

Figure 6:
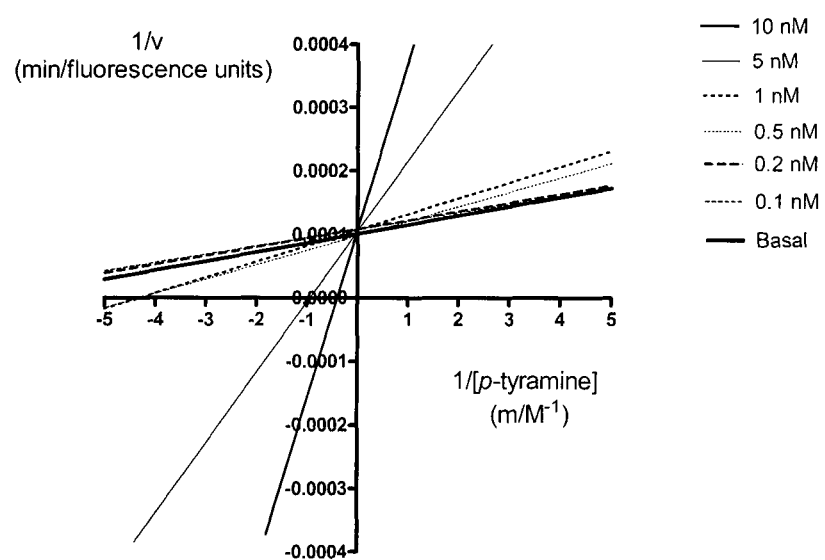
FIG. 6 shows results of the substrate-dependent inhibition experiments for investigation the mode of MAO-B inhibition using recombinant human MAO-B enzyme in the presence of different concentrations of N-(3,4-dichlorophenyl)-1-methyl-1H-indazole-5-carboxamide with p-tyramine (0.05, 0.1, 0.25, 0.5, 1.0 and 1.5 mM) as substrate (n=2).

The results of the substrate-dependent inhibition experiments are illustrated in FIG. 6.

The compounds of Examples 1-26 of the present invention are selective and highly potent inhibitors of rat and human MAO-B with $IC_{50}$ values in the subnanomolar range, as shown in Table 2. The compound numbers in Table 3 are the same that in the preparative Examples above.

TABLE 3
| Example/Compound | rat MAO-A (rat liver mitochondria) IC$_{50}$ (nM) (% inhibition at 10 μM) | rat MAO-B (rat liver mitochondria) IC$_{50}$ (nM) | human MAO-A IC$_{50}$ (nM) (% inhibition at 10 μM) | human MAO-B IC$_{50}$ (nM) |
|---|---|---|---|---|
| 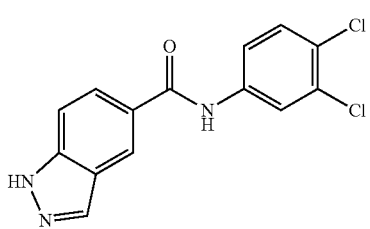 1 | >10000 (42 ± 4) | 1.43 ± 0.11 | ≥10000 (46 ± 2) | 0.586 ± 0.087 |
| 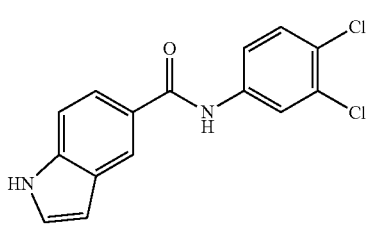 [SMILES: O=C(Nc1ccc(Cl)c(Cl)c1)c1ccc2[nH]ccc2c1] 2 | 6790 ± 121 (70 ± 1) | 1.01 ± 0.16 | 1300 ± 68 (88 ± 1) | 0.227 ± 0.039 |
| 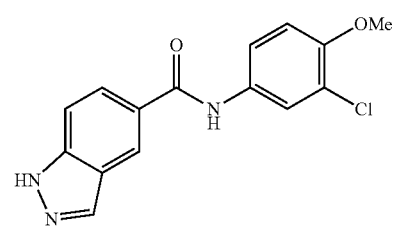 [SMILES: COc1ccc(NC(=O)c2ccc3[nH]ncc3c2)cc1Cl] 3 | >10000 (13 ± 2) | 21.9 ± 3.4 | >10000 (30 ± 2) | 3.42 ± 0.28 |
| 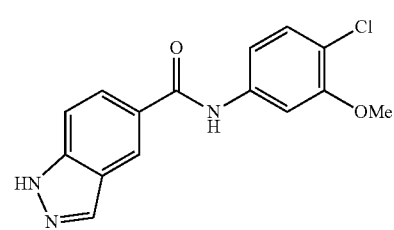 [SMILES: COc1cc(NC(=O)c2ccc3[nH]ncc3c2)ccc1Cl] 4 | >10000 (24 ± 1) | 43.1 ± 4.2 | 8790 ± 200 (62 ± 5) | 4.36 ± 0.08 |
| 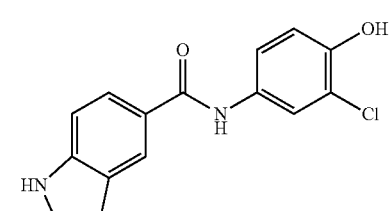 5 | <10000 (60 ± 1) | 941 ± 51 | >10000 (33 ± 1) | 123 ± 16 |

TABLE 3-continued
| Example/Compound | rat MAO-A (rat liver mitochondria) IC$_{50}$ (nM) (% inhibition at 10 μM) | rat MAO-B (rat liver mitochondria) IC$_{50}$ (nM) | human MAO-A IC$_{50}$ (nM) (% inhibition at 10 μM) | human MAO-B IC$_{50}$ (nM) |
|---|---|---|---|---|
| 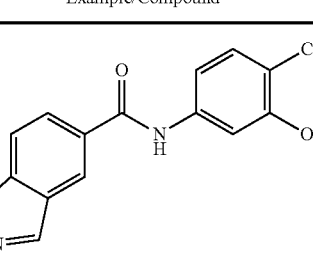 6 | >10000 (43 ± 1) | 385 ± 9 | 3000 ± 122 (81 ± 3) | 37.5 ± 7.3 |
| 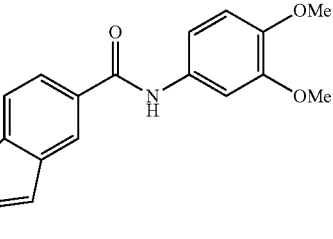 7 | >10000 (9 ± 2) | 1400 ± 56 | >10000 (9 ± 2) | 185 ± 21 |
| 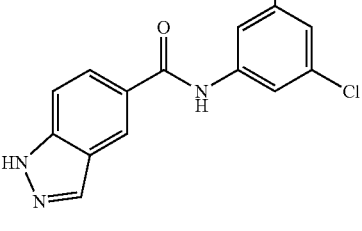 [SMILES: O=C(Nc1ccc(F)c(Cl)c1)c1ccc2[nH]ncc2c1] 8 | >10000 (5 ± 0) | 2.73 ± 0.21 | <10000 (65 ± 0) | 2.75 ± 0.40 |
| 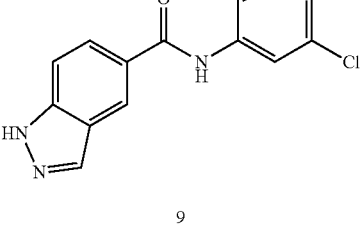 9 | >10000 (17 ± 0) | 2.36 ± 0.17 | >10000 (40 ± 0) | 0.679 ± 0.044 |
| 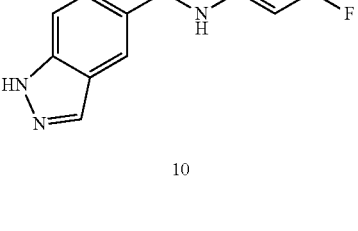 10 | >10000 (30 ± 2) | 2.61 ± 0.68 | <10000 (55 ± 2) | 0.668 ± 0.053 |

TABLE 3-continued
| Example/Compound | rat MAO-A (rat liver mitochondria) IC$_{50}$ (nM) (% inhibition at 10 μM) | rat MAO-B (rat liver mitochondria) IC$_{50}$ (nM) | human MAO-A IC$_{50}$ (nM) (% inhibition at 10 μM) | human MAO-B IC$_{50}$ (nM) |
|---|---|---|---|---|
| 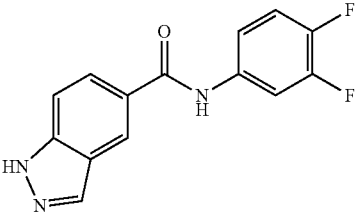 [SMILES: O=C(Nc1ccc(F)c(F)c1)c1ccc2[nH]ncc2c1] 11 | >10000 (13 ± 0) | 8.89 ± 0.05 | >10000 (36 ± 0) | 1.59 ± 0.16 |
| 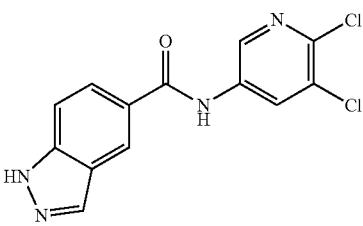 [SMILES: O=C(Nc1cnc(Cl)c(Cl)c1)c1ccc2[nH]ncc2c1] 12 | <10000 (59 ± 2) | 26.6 ± 1.5 | <10000 (52 ± 5) | 5.42 ± 0.20 |
| 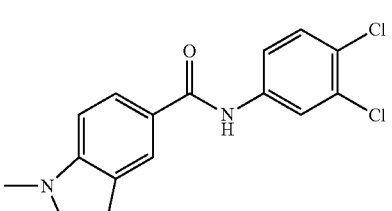 13 | >10000 (42 ± 1) | 1.32 ± 0.09 | >10000 (37 ± 8) | 0.386 ± 0.052 |
| 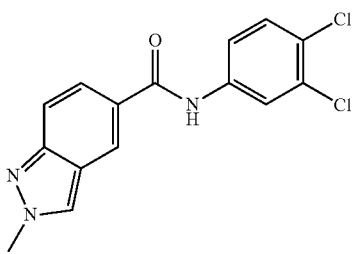 14 | 1740 ± 60 | 22.5 ± 0.6 | 420 ± 24 | 1.44 ± 0.41 |
| 15 (b cmec, 13/14 = 4.7:1) | >10000 (27 ± 1) | 5.57 ± 0.65 | <10000 (62 ± 5) | 1.87 ± 0.12 |
| 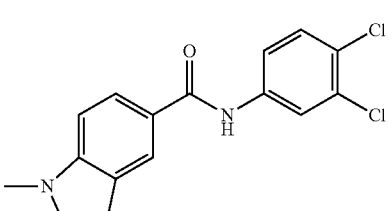 16 | >10000 (3 ± 1) | 1.11 ± 0.11 | >10000 (13 ± 5) | 2.26 ± 0.16 |

TABLE 3-continued
| Example/Compound | rat MAO-A (rat liver mitochondria) IC$_{50}$ (nM) (% inhibition at 10 μM) | rat MAO-B (rat liver mitochondria) IC$_{50}$ (nM) | human MAO-A IC$_{50}$ (nM) (% inhibition at 10 μM) | human MAO-B IC$_{50}$ (nM) |
|---|---|---|---|---|
| 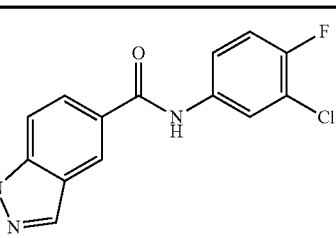 17 | >10000 (29 ± 8) | 1.36 ± 0.13 | >10000 (53 ± 2) | 0.662 ± 0.06 |
| 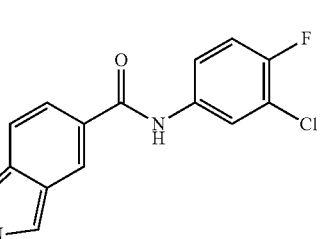 18 | 1690 ± 143 (90 ± 3) | 20.3 ± 3.0 | 562 ± 62 (95 ± 0) | 8.08 ± 1.05 |
| 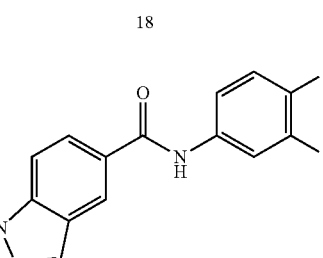 19 | >10000 (18 ± 10) | 5.65 ± 0.48 | >10000 (46 ± 0) | 1.52 ± 0.18 |
| 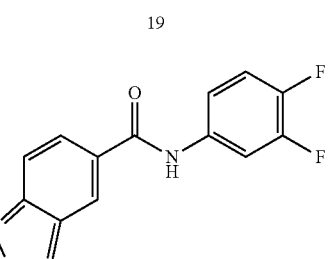 20 | 1880 ± 93 (83 ± 3) | 221 ± 21 | 764 ± 40 | 38.4 ± 1.80 |
| 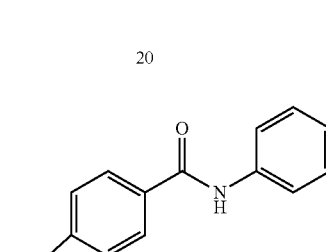 21 | <10000 (57 ± 1) | 3.82 ± 0.22 | 2870 ± 218 (81 ± 0) | 1.08 ± 0.08 |

TABLE 3-continued
| Example/Compound | rat MAO-A (rat liver mitochondria) IC$_{50}$ (nM) (% inhibition at 10 μM) | rat MAO-B (rat liver mitochondria) IC$_{50}$ (nM) | human MAO-A IC$_{50}$ (nM) (% inhibition at 10 μM) | human MAO-B IC$_{50}$ (nM) |
|---|---|---|---|---|
| 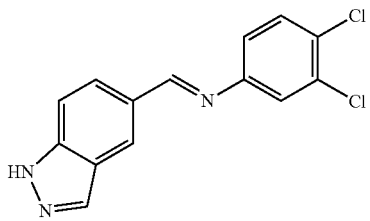 [SMILES: Clc1ccc(/N=C/c2ccc3[nH]ncc3c2)cc1Cl] 22 | >10000 (43 ± 3) | 3.69 ± 0.17 | <10000 (62 ± 2) | 0.612 ± 0.065 |
| 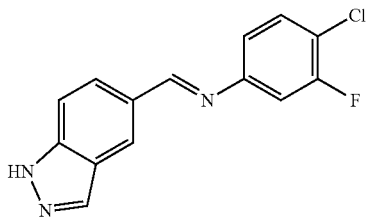 23 | >10000 (27 ± 0) | 25.2 ± 0.11 | >10000 (44 ± 4) | 1.91 ± 0.27 |
| 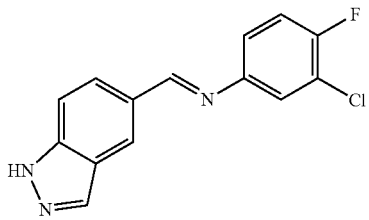 [SMILES: Fc1ccc(/N=C/c2ccc3[nH]ncc3c2)cc1Cl] 24 | >10000 (35 ± 0) | 6.08 ± 0.52 | <10000 (54 ± 2) | 2.10 ± 0.30 |
| 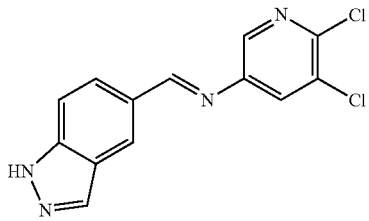 25 | >10000 (45 ± 0) | 1.48 ± 0.07 | <10000 (67 ± 2) | 0.474 ± 0.02 |
| 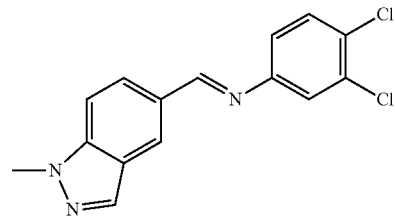 [SMILES: Cn1ncc2cc(/C=N/c3ccc(Cl)c(Cl)c3)ccc21] 26 | >10000 (23 ± 3) | 4.55 ± 0.31 | <10000 (57 ± 1) | 1.03 ± 0.09 |

FIGS. 1-4 illustrated the mean inhibition curves for two representative compounds of the present invention in functional MAO-B assays. More specifically, FIG. 1 shows the mean inhibition curve of the MAO-B assay at rat liver mitochondria (pre-treated with clorgyline 30 nM) of N-(3,4-dichlorophenyl)-1H-indazole-5-carboxamide (compound No 1 in Table 3). The estimated $IC_{50}$ value at rat MAO-B is 1.43±0.11 nM.

Figure 2:
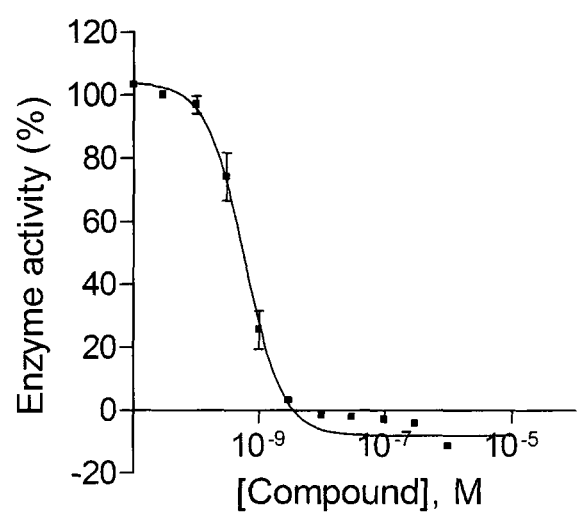
FIG. 2 shows the mean inhibition curve of the human MAO-B assay for determination of MAO-B inhibition activity ($IC_{50}$) of N-(3,4-dichlorophenyl)-1H-indazole-5-carboxamide.

FIG. 2 shows the mean inhibition curve of the recombinant human MAO-B assay of N-(3,4-dichlorophenyl)-1H-indazole-5-carboxamide (compound No 1 in Table 3). The estimated $IC_{50}$ value at human MAO-B is 0.586±0.087 nM.

Figure 3:
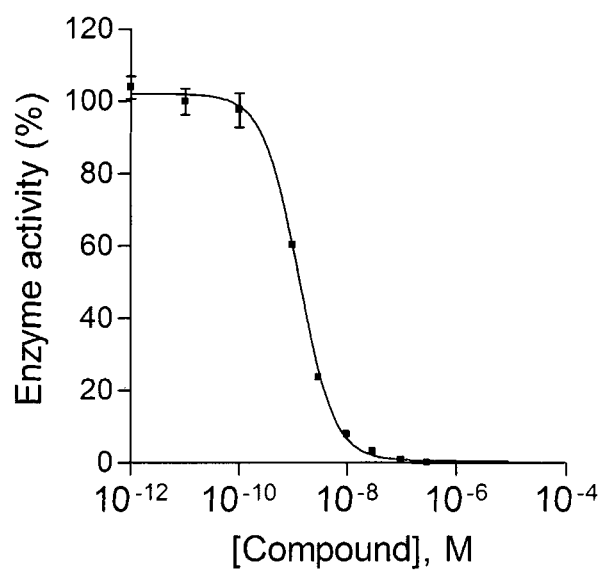
FIG. 3 shows the mean inhibition curve of the rat MAO-B assay using rat liver mitochondria (pre-treated with chlorgiline 30 nM) for determination of MAO-B inhibition activity ($IC_{50}$) of N-(3,4-dichlorophenyl)-1-methyl-1H-indazole-5-carboxamide.

FIG. 3 shows the mean inhibition curve of the MAO-B assay at rat liver mitochondria (pre-treated with clorgyline 30 nM) of N-(3,4-dichlorophenyl)-1-methyl-1H-indazole-5-carboxamide (compound No 13 in Table 3). The estimated $IC_{50}$ value at rat MAO-B is 1.32±0.09 nM.

Figure 4:
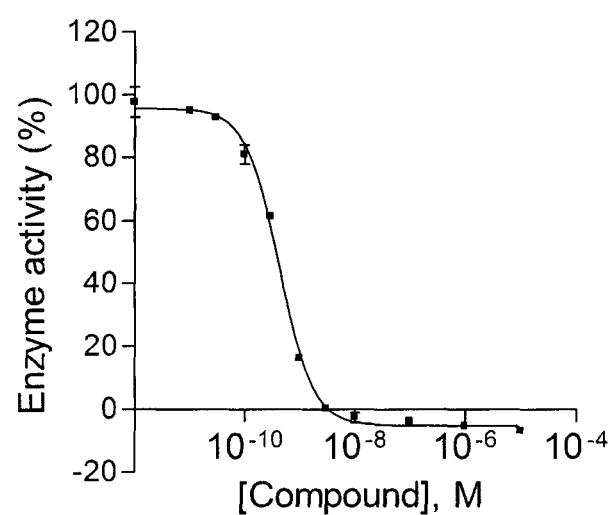
FIG. 4 shows the mean inhibition curve of the human MAO-B assay for determination of MAO-B inhibition activity ($IC_{50}$) of N-(3,4-dichlorophenyl)-1-methyl-1H-indazole-5-carboxamide.

FIG. 4 shows the mean inhibition curve of the recombinant human MAO-B assay of N-(3,4-dichlorophenyl)-1-methyl-1H-indazole-5-carboxamide (compound No 13 in Table 3). The estimated $IC_{50}$ value at human MAO-B is 0.386±0.052.

The invention claimed is:

1. A substituted indazole derivative selected from the group consisting of
N-(3,4-Dichlorophenyl)-1H-indazole-5-carboxamide,
N-(3,4-Dichlorophenyl)-1H-indole-5-carboxamide,
N-(3-Chloro-4-methoxyphenyl)-1H-indazole-5-carboxamide,
N-(4-Chloro-3-methoxyphenyl)-1H-indazole-5-carboxamide,
N-(3-Chloro-4-hydroxyphenyl)-1H-indazole-5-carboxamide,
N-(4-Chloro-3-hydroxyphenyl)-1H-indazole-5-carboxamide,
N-(3,4-Dimethoxyphenyl)-1H-indazole-5-carboxamide,
N-(3,5-Dichlorophenyl)-1H-indazole-5-carboxamide,
N-(3-Chloro-4-fluorophenyl)-1H-indazole-5-carboxamide,
N-(4-Chloro-3-fluorophenyl)-1H-indazole-5-carboxamide,
N-(3,4-Difluorophenyl)-1H-indazole-5-carboxamide,
N-(5,6-Dichloropyridin-3-yl)-1H-indazole-5-carboxamide,
N-(3,4-Dichlorophenyl)-1-methyl-1H-indazole-5-carboxamide,
N-(3,4-Dichlorophenyl)-2-methyl-2H-indazole-5-carboxamide,
mixture of N-(3,4-Dichlorophenyl)-1-methyl-1H-indazole-5-carboxamide and
N-(3,4-Dichlorophenyl)-2-methyl-2H-indazole-5-carboxamide,
N-(3,4-Dichlorophenyl)-1-methyl-1H-indole-5-carboxamide,
N-(3-Chloro-4-fluorophenyl)-1-methyl-1H-indazole-5-carboxamide,
N-(3-Chloro-4-fluorophenyl)-2-methyl-2H-indazole-5-carboxamide,
N-(3,4-Difluorophenyl)-1-methyl-1H-indazole-5-carboxamide,
N-(3,4-Difluorophenyl)-2-methyl-2H-indazole-5-carboxamide,
N-(3,4-dichlorophenyl)-1-(2-methoxyethyl)-1H-indazole-5-carboxamide,
(E)-N-((1H-indazol-5-yl)methylene)-3,4-dichloroaniline,
(E)-N-((1H-indazol-5-yl)methylene)-4-chloro-3-fluoroaniline,
(E)-N-((1H-indazol-5-yl)methylene)-3-chloro-4-fluoroaniline,
(E)-N-((1H-indazol-5-yl)methylene)-5,6-dichloropyridin-3-amine, and
(E)-3,4-dichloro-N-((1-methyl-1H-indazol-5-yl)methylene)aniline.

* * * * *